(12) United States Patent
Saikrishnan et al.

(10) Patent No.: US 11,071,627 B2
(45) Date of Patent: *Jul. 27, 2021

(54) ORTHOGONALLY DELIVERED TRANSCATHETER HEART VALVE FRAME FOR VALVE IN VALVE PROSTHESIS

(71) Applicant: VDyne, Inc., Maple Grove, MN (US)

(72) Inventors: Neelakantan Saikrishnan, Plymouth, MN (US); Mark Christianson, Plymouth, MN (US); Robert Vidlund, Forest Lake, MN (US)

(73) Assignee: VDyne, Inc., Maple Grove, MN (US)

( * ) Notice: Subject to any disclaimer, the term of this patent is extended or adjusted under 35 U.S.C. 154(b) by 228 days.

This patent is subject to a terminal disclaimer.

(21) Appl. No.: 16/163,577

(22) Filed: Oct. 18, 2018

(65) Prior Publication Data
US 2020/0121452 A1 Apr. 23, 2020

(51) Int. Cl.
*A61F 2/24* (2006.01)
(52) U.S. Cl.
CPC ............ *A61F 2/243* (2013.01); *A61F 2/2418* (2013.01); *A61F 2/2469* (2013.01); *A61F 2/2403* (2013.01); *A61F 2/2439* (2013.01)
(58) Field of Classification Search
CPC ..... A61F 2/24–2496; A61B 2017/0419; A61B 2018/0038
See application file for complete search history.

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 6,006,134 A | 12/1999 | Hill et al. |
| 6,197,013 B1 | 3/2001 | Reed et al. |
| 6,290,719 B1 | 9/2001 | Garberoglio |

(Continued)

FOREIGN PATENT DOCUMENTS

| | | |
|---|---|---|
| AU | 2006203686 B2 | 11/2008 |
| AU | 2009219415 A1 | 9/2009 |

(Continued)

OTHER PUBLICATIONS

International Search Report and Written Opinion for International Application No. PCT/US2019/028822, dated Oct. 24, 2019, 14 pages.

(Continued)

*Primary Examiner* — Tan-Uyen T Ho
*Assistant Examiner* — Charles M Wei

(57) ABSTRACT

The invention relates to a transcatheter heart valve replacement (A62F2/2412), and in particular an orthogonally delivered transcatheter prosthetic valve frame having a tubular frame for mounting a flow control component wherein the valve frame is compressible to a compressed configuration for sideways or lateral introduction into the body using a delivery catheter for implanting at a desired location in the body, where the compressed configuration has a long-axis oriented roughly perpendicular to the central axis of the native annulus, wherein the long-axis of the compressed configuration of the valve is substantially parallel to a length-wise cylindrical axis of the delivery catheter, and wherein the valve has a height of about 5-60 mm and a diameter of about 25-80 mm.

18 Claims, 23 Drawing Sheets

(56) References Cited

U.S. PATENT DOCUMENTS

| | | |
|---|---|---|
| 6,449,507 B1 | 9/2002 | Hill et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,374,571 B2 | 5/2008 | Pease et al. |
| 7,449,027 B2 | 11/2008 | Hunt et al. |
| 7,717,952 B2 | 5/2010 | Case et al. |
| 7,749,245 B2 | 7/2010 | Cohn et al. |
| 7,753,949 B2 | 7/2010 | Lamphere et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 * | 2/2018 | Costello ............... A61F 2/2412 |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,333 B2 | 3/2019 | Cartledge |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 * | 6/2019 | Christianson ......... A61F 2/2409 |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |

(56) References Cited

U.S. PATENT DOCUMENTS

| | | |
|---|---|---|
| 10,595,994 B1 | 3/2020 | Christianson et al. |
| 10,631,983 B1 | 4/2020 | Christianson et al. |
| 10,653,522 B1 * | 5/2020 | Vidlund .............. A61F 2/2433 |
| 10,758,346 B1 * | 9/2020 | Christianson ........ A61F 2/2418 |
| 2003/0040772 A1 | 2/2003 | Hyodoh et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0088047 A1 | 5/2004 | Spence et al. |
| 2004/0116996 A1 | 6/2004 | Freitag |
| 2004/0199209 A1 | 10/2004 | Hill et al. |
| 2005/0010246 A1 | 1/2005 | Streeter et al. |
| 2005/0107811 A1 | 5/2005 | Starksen et al. |
| 2005/0137686 A1 | 6/2005 | Salahieh et al. |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0271098 A1 | 11/2006 | Peacock, III |
| 2006/0276887 A1 | 12/2006 | Brady et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | MacAulay et al. |
| 2010/0049294 A1 | 2/2010 | Zukowski et al. |
| 2010/0049313 A1 | 2/2010 | Alon |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0305685 A1 | 12/2010 | Millwee et al. |
| 2011/0029071 A1 | 2/2011 | Zlotnick et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0331929 A1 | 12/2013 | Mitra et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 * | 8/2014 | Kovalsky .............. A61F 2/2418 623/2.17 |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0371789 A1 | 12/2014 | Hariton et al. |
| 2014/0379076 A1 | 12/2014 | Vidlund |
| 2015/0005808 A1 | 1/2015 | Chouinard et al. |
| 2015/0005874 A1 | 1/2015 | Vidlund et al. |
| 2015/0039081 A1 * | 2/2015 | Costello ................ A61F 2/2412 623/2.11 |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |

(56) References Cited

U.S. PATENT DOCUMENTS

| | | |
|---|---|---|
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0181851 A1 | 6/2017 | Annest |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson |
| 2017/0348100 A1 | 12/2017 | Lane et al. |
| 2017/0360558 A1 | 12/2017 | Ma |
| 2017/0360561 A1 | 12/2017 | Bell et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |

(56) References Cited

U.S. PATENT DOCUMENTS

| | | |
|---|---|---|
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1* | 7/2018 | Chambers ............. A61F 2/2418 |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296335 A1 | 10/2018 | Miyashiro |
| 2018/0296337 A1 | 10/2018 | Duhay et al. |
| 2018/0303488 A1 | 10/2018 | Hill |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0388219 A1 | 12/2019 | Lane et al. |
| 2020/0121458 A1* | 4/2020 | Vidlund ................ A61F 2/2436 |
| 2020/0179146 A1 | 6/2020 | Christianson et al. |
| 2020/0188027 A1 | 6/2020 | Perrin et al. |
| 2020/0237506 A1* | 7/2020 | Christianson .......... B33Y 80/00 |
| 2020/0289259 A1 | 9/2020 | Christianson et al. |
| 2020/0289263 A1* | 9/2020 | Christianson ......... A61F 2/2433 |
| 2021/0000592 A1 | 1/2021 | Christianson et al. |
| 2021/0137677 A1 | 5/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |

(56) References Cited

FOREIGN PATENT DOCUMENTS

| | | |
|---|---|---|
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |

(56) References Cited

FOREIGN PATENT DOCUMENTS

| | | |
|---|---|---|
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | 0044308 A2 | 8/2000 |
| WO | 03072287 A1 | 9/2003 |
| WO | 2004093728 A2 | 11/2004 |
| WO | 2006029062 A1 | 3/2006 |
| WO | 2006066150 A2 | 6/2006 |

(56) References Cited

FOREIGN PATENT DOCUMENTS

| | | |
|---|---|---|
| WO | 2007047945 A2 | 4/2007 |
| WO | 2007054015 A1 | 5/2007 |
| WO | 2007095233 A2 | 8/2007 |
| WO | 2007129220 A2 | 11/2007 |
| WO | 2008013915 A2 | 1/2008 |
| WO | 2008091925 A2 | 7/2008 |
| WO | 2008103280 A2 | 8/2008 |
| WO | 2009081396 A2 | 7/2009 |
| WO | 2009094188 A2 | 7/2009 |
| WO | 2009094189 A1 | 7/2009 |
| WO | 2009094197 A1 | 7/2009 |
| WO | 2009094501 A1 | 7/2009 |
| WO | 2009100242 A2 | 8/2009 |
| WO | 2010029190 A1 | 3/2010 |
| WO | 2010119110 A1 | 10/2010 |
| WO | 2011112706 A2 | 9/2011 |
| WO | 2011137531 A1 | 11/2011 |
| WO | 2012009558 A2 | 1/2012 |
| WO | WO 2012/035279 | 3/2012 |
| WO | 2012063228 A1 | 5/2012 |
| WO | 2012063242 A1 | 5/2012 |
| WO | 2012112469 A2 | 8/2012 |
| WO | 2012145545 A1 | 10/2012 |
| WO | 2012161786 A1 | 11/2012 |
| WO | 2012175483 A1 | 12/2012 |
| WO | 2012178115 A2 | 12/2012 |
| WO | 2013021375 A2 | 2/2013 |
| WO | 2013085719 A1 | 6/2013 |
| WO | 2013103612 A1 | 7/2013 |
| WO | 2013116785 A1 | 8/2013 |
| WO | 2013128436 A1 | 9/2013 |
| WO | 2013148019 A1 | 10/2013 |
| WO | 2013166356 A2 | 11/2013 |
| WO | 2013177684 A1 | 12/2013 |
| WO | 2013184945 A1 | 12/2013 |
| WO | 2014011330 A1 | 1/2014 |
| WO | 2014064695 A2 | 5/2014 |
| WO | 2014121042 A1 | 8/2014 |
| WO | 2014133667 A1 | 9/2014 |
| WO | 2014137805 A1 | 9/2014 |
| WO | 2014140230 A1 | 9/2014 |
| WO | 2014162306 A2 | 10/2014 |
| WO | 2014164151 A1 | 10/2014 |
| WO | 2014168655 A1 | 10/2014 |
| WO | 2015004173 A1 | 1/2015 |
| WO | 2015014960 A1 | 2/2015 |
| WO | 2015017075 A1 | 2/2015 |
| WO | 2015055605 A1 | 4/2015 |
| WO | 2015057735 A1 | 4/2015 |
| WO | 2015058039 A1 | 4/2015 |
| WO | 2015061021 A1 | 4/2015 |
| WO | 2015117025 A1 | 8/2015 |
| WO | 2015120122 A2 | 8/2015 |
| WO | 2015123607 A2 | 8/2015 |
| WO | 2015127264 A1 | 8/2015 |
| WO | 2015142834 A1 | 9/2015 |
| WO | 2015153755 A2 | 10/2015 |
| WO | 2016011267 A1 | 1/2016 |
| WO | 2016025733 A1 | 2/2016 |
| WO | 2016083351 A1 | 6/2016 |
| WO | 2016097337 A1 | 6/2016 |
| WO | 2016100799 A1 | 6/2016 |
| WO | 2016118851 A1 | 7/2016 |
| WO | 2016130913 A1 | 8/2016 |
| WO | 2016148777 A1 | 9/2016 |
| WO | 2016149083 A1 | 9/2016 |
| WO | 2016150806 A1 | 9/2016 |
| WO | 2016189391 A2 | 12/2016 |
| WO | 2017040684 A1 | 3/2017 |
| WO | 2017096157 A1 | 6/2017 |
| WO | 2017114928 A1 | 7/2017 |
| WO | 2017120404 A1 | 7/2017 |
| WO | 2017121193 A1 | 7/2017 |
| WO | 2017121194 A1 | 7/2017 |
| WO | 2017121195 A1 | 7/2017 |
| WO | 2017136596 A1 | 8/2017 |
| WO | 2017151292 A1 | 9/2017 |
| WO | 2017155892 A1 | 9/2017 |
| WO | 2017156352 A1 | 9/2017 |
| WO | 2017161204 A1 | 9/2017 |
| WO | 2017165842 A1 | 9/2017 |
| WO | 2017196511 A1 | 11/2017 |
| WO | 2017201082 A1 | 11/2017 |
| WO | 2017202042 A1 | 11/2017 |
| WO | 2017210356 A1 | 12/2017 |
| WO | 2017218375 A1 | 12/2017 |
| WO | 2018008019 A2 | 1/2018 |
| WO | 2018026445 A1 | 2/2018 |
| WO | 2018026904 A1 | 2/2018 |
| WO | 2018035105 A1 | 2/2018 |
| WO | 2018040244 A1 | 3/2018 |
| WO | 2018042439 A1 | 3/2018 |
| WO | 2018045156 A2 | 3/2018 |
| WO | 2018071115 A1 | 4/2018 |
| WO | 2018077143 A1 | 5/2018 |
| WO | 2018077146 A1 | 5/2018 |
| WO | 2018080328 A1 | 5/2018 |
| WO | 2018083493 A1 | 5/2018 |
| WO | 2018090576 A1 | 5/2018 |
| WO | 2018098032 A1 | 5/2018 |
| WO | 2018106460 A1 | 6/2018 |
| WO | 2018119304 A1 | 6/2018 |
| WO | 2018138658 A1 | 8/2018 |
| WO | 2018145055 A1 | 8/2018 |
| WO | 2018156767 A1 | 8/2018 |
| WO | 2018156922 A1 | 8/2018 |
| WO | 2018158747 A1 | 9/2018 |
| WO | 2018160790 A1 | 9/2018 |
| WO | 2018165358 A1 | 9/2018 |
| WO | 2018170149 A1 | 9/2018 |
| WO | 2018175220 A1 | 9/2018 |
| WO | 2018175619 A1 | 9/2018 |
| WO | 2018178208 A1 | 10/2018 |
| WO | 2018178977 A1 | 10/2018 |
| WO | 2018183832 A1 | 10/2018 |
| WO | 2018184225 A1 | 10/2018 |
| WO | 2018184226 A1 | 10/2018 |
| WO | 2018187495 A1 | 10/2018 |
| WO | 2018187753 A1 | 10/2018 |
| WO | 2018191681 A1 | 10/2018 |
| WO | 2018200531 A1 | 11/2018 |
| WO | 2018200942 A2 | 11/2018 |
| WO | 2018201111 A2 | 11/2018 |
| WO | 2018201212 A1 | 11/2018 |
| WO | 2018204106 A1 | 11/2018 |
| WO | 2018209302 A1 | 11/2018 |
| WO | 2018213209 A1 | 11/2018 |
| WO | 2018217525 A1 | 11/2018 |
| WO | 2018222799 A1 | 12/2018 |
| WO | 2018226628 A1 | 12/2018 |
| WO | 2019003221 A1 | 1/2019 |
| WO | 2019006383 A2 | 1/2019 |
| WO | 2019010458 A1 | 1/2019 |
| WO | 2019014473 A1 | 1/2019 |
| WO | 2019018319 A1 | 1/2019 |
| WO | 2019023385 A1 | 1/2019 |
| WO | 2019026059 A1 | 2/2019 |
| WO | 2019032992 A2 | 2/2019 |
| WO | 2019037579 A1 | 2/2019 |
| WO | 2019040357 A1 | 2/2019 |
| WO | 2019042472 A1 | 3/2019 |
| WO | 2019046099 A1 | 3/2019 |
| WO | 2019046205 A1 | 3/2019 |
| WO | 2019051168 A2 | 3/2019 |
| WO | 2019051180 A2 | 3/2019 |
| WO | 2019051587 A1 | 3/2019 |
| WO | 2019055577 A1 | 3/2019 |
| WO | 2019058178 A1 | 3/2019 |
| WO | 2019067219 A1 | 4/2019 |
| WO | 2019081689 A1 | 5/2019 |
| WO | 2019081985 A2 | 5/2019 |
| WO | 2019086958 A1 | 5/2019 |
| WO | 2019089136 A1 | 5/2019 |
| WO | 2019089821 A1 | 5/2019 |

(56) References Cited

FOREIGN PATENT DOCUMENTS

| | | |
|---|---|---|
| WO | 2019093387 A1 | 5/2019 |
| WO | 2019095049 A1 | 5/2019 |
| WO | 2019096033 A1 | 5/2019 |
| WO | 2019099722 A2 | 5/2019 |
| WO | 2019116322 A1 | 6/2019 |
| WO | 2019119674 A1 | 6/2019 |
| WO | 2019126518 A1 | 6/2019 |
| WO | 2019131148 A1 | 7/2019 |
| WO | 2019136162 A1 | 7/2019 |
| WO | 2019140293 A1 | 7/2019 |
| WO | 2019143775 A1 | 7/2019 |
| WO | 2019144036 A1 | 7/2019 |
| WO | 2019147585 A1 | 8/2019 |
| WO | 2019165213 A1 | 8/2019 |
| WO | 2019173475 A1 | 9/2019 |
| WO | 2019190800 A1 | 10/2019 |
| WO | 2019191102 A1 | 10/2019 |
| WO | WO 2019/195860 | 10/2019 |

OTHER PUBLICATIONS

Office Action for U.S. Appl. No. 17/167,983, dated Apr. 13, 2021, 20 pages.
Office Action for U.S. Appl. No. 17/154,438, dated May 3, 2021, 16 pages.
Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
Office Action for U.S. Appl. No. 16/445,210, dated Jan. 28, 2021, 7 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/448,108, dated Mar. 8, 2021, 8 pages.
Office Action for U.S. Appl. No. 17/154,227, dated Mar. 29, 2021, 6 pages.
International Search Report and Written Opinion for International Application No. PCT/US2021/013570, dated Apr. 1, 2021, 9 pages.

\* cited by examiner

FIG. 33
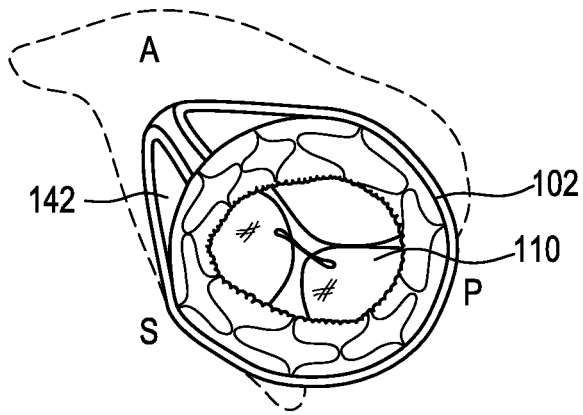
FIG. 34  FIG. 35
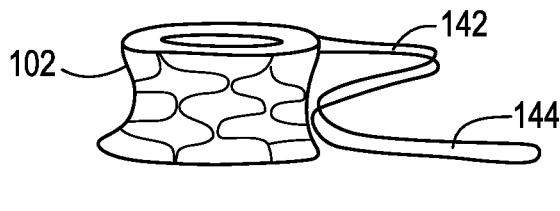 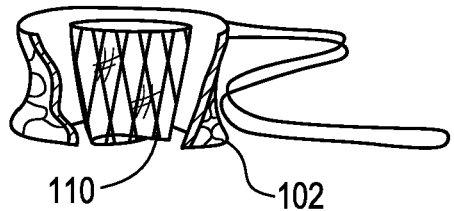
FIG. 36
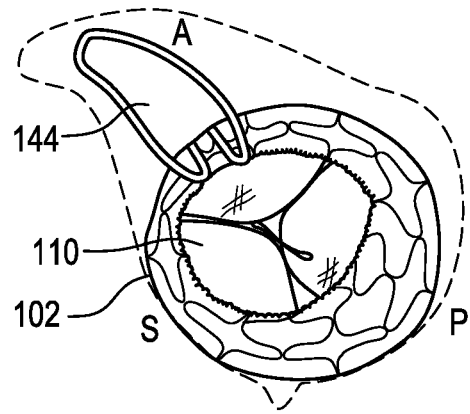

ORTHOGONALLY DELIVERED TRANSCATHETER HEART VALVE FRAME FOR VALVE IN VALVE PROSTHESIS

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to an Orthogonally Delivered Transcatheter Heart Valve Frame for Valve in Valve Prosthesis (A62F2/2412).

Description of the Related Art

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting dic technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

Accordingly, the present invention is directed to an orthogonally delivered transcatheter prosthetic valve frame for a valve in valve prosthesis system, comprising: a tubular frame having a central lumen defined by an inner circumferential surface of the tubular frame, said tubular frame having an outer circumferential surface for engaging native annular tissue, wherein the tubular frame is compressible to a compressed orthogonal configuration for sideways or lateral (orthogonal) introduction into the body using a delivery catheter for implanting at a desired location in the body, said compressed orthogonal configuration having a horizontal long-axis oriented at an intersecting angle roughly perpendicular, e.g. about 90 degrees, but ranging from 45-135 degrees, to a vertical axis of the central lumen, and expandable to an expanded configuration having a horizontal long-axis oriented at an intersecting angle roughly perpendicular, e.g. about 90 degrees, but ranging from of between 45-135 degrees to the vertical axis of the central lumen, wherein the horizontal long-axis of the compressed configuration of the tubular frame is substantially parallel to a length-wise cylindrical axis of the delivery catheter, wherein the tubular frame has a height of about 5-60 mm and a diameter of about 25-80 mm.

In another preferred embodiment of the invention, there is provided a valve frame wherein the tubular frame forms a two part framework, a first part comprises a flared atrial cuff joined to a second part that comprises a trans-annular tubular segment, wherein the cuff is joined to the trans-annular tubular segment around the circumference of a top edge of the trans-annular tubular segment.

In another preferred embodiment of the invention, there is provided a valve frame wherein said tubular frame is comprised of a braided, wire, or laser-cut wire frame, and said tubular frame is covered with a biocompatible material.

In another preferred embodiment of the invention, there is provided a valve frame wherein the tubular frame has a side profile of a flat cone shape having a diameter R of 40-80 mm, a diameter r of 20-60 mm, and a height of 5-60 mm.

In another preferred embodiment of the invention, there is provided a valve frame wherein the tubular frame has the inner circumferential surface and an outer circumferential surface, said inner circumferential surface and said outer circumferential surface covered with a biocompatible material selected from the following consisting of: the inner surface covered with pericardial tissue, the outer circumferential surface covered with a woven synthetic polyester material, and both the inner surface covered with pericardial tissue and the outer circumferential surface covered with a woven synthetic polyester material.

In another preferred embodiment of the invention, there is provided a valve frame wherein the tubular frame has a side profile of an hourglass shape having a top diameter R1 of 40-80 mm, a bottom diameter R2 of 50-70 mm, an internal diameter r of 20-60 mm, and a height of 5-60 mm.

In another preferred embodiment of the invention, there is provided a valve frame wherein the valve in an expanded configuration has a central tube axis that is substantially parallel to the first direction.

In another preferred embodiment of the invention, there is provided a valve frame additionally comprising a flow control component having an internal diameter of 20-60 mm and a height of 10-40 mm, and a plurality of leaflets of pericardial material joined to form a rounded cylinder at an inflow end and having a closable aperture at an outflow end.

In another preferred embodiment of the invention, there is provided a valve frame wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battons, rigid or semi-rigid panels, and combinations thereof.

In another preferred embodiment of the invention, there is provided a valve frame having a tension arm extending from a distal side of the tubular frame, the tension arm comprised of wire loop or wire frame, integrated frame section, or stent, extending from about 10-40 mm away from the tubular frame.

In another preferred embodiment of the invention, there is provided a valve frame having (i) an upper tension arm attached to a distal upper edge of the tubular frame, the upper tension arm comprised of wire loop or wire frame extending from about 2-20 mm away from the tubular frame, and (ii) a lower tension arm extending from a distal side of the tubular frame, the lower tension arm comprised of wire loop or wire frame, integrated frame section, or stent, extending from about 10-40 mm away from the tubular frame.

In another preferred embodiment of the invention, there is provided a valve frame having at least one tissue anchor connected to the tubular frame for engaging native tissue.

In another preferred embodiment of the invention, there is provided a method for orthogonal delivery of an implantable prosthetic valve frame to a desired location in the body for a valve prosthesis system, the method comprising the steps:
  (i) advancing a delivery catheter to the desired location in the body and delivering an expandable prosthetic valve frame to the desired location in the body by releasing the valve frame from the delivery catheter, wherein the valve frame comprises a tubular frame having a central lumen defined by an inner circumferential surface of the tubular frame, said tubular frame having an outer circumferential surface for engaging native annular tissue, wherein the tubular frame is compressible to a compressed orthogonal configuration for introduction into the body using a delivery catheter for implanting at a desired location in the body, said compressed orthogonal configuration having a horizontal long-axis oriented at an intersecting angle roughly perpendicular, e.g. 90 degrees, but ranging from between 45-135 degrees to a vertical axis of the central lumen, and expandable to an expanded configuration having a horizontal long-axis oriented at an intersecting angle roughly perpendicular, e.g. 90 degrees, but ranging from between 45-135 degrees to the vertical axis of the central lumen, wherein the horizontal long-axis of the compressed configuration of the tubular frame is substantially parallel to a length-wise cylindrical axis of the delivery catheter, wherein the tubular frame has a height of about 5-60 mm and a diameter of about 25-80 mm; and
  (ii) advancing a second delivery catheter to the desired location in the body and delivering an expandable prosthetic valve to the central lumen of the valve frame, expanding the expandable prosthetic valve within the central lumen to mount the prosthetic valve within the valve frame, wherein the prosthetic valve is delivered and expanded parallel to the vertical axis of the central lumen, and releasing the prosthetic valve from the second delivery catheter.

In another preferred embodiment of the invention, there is provided a delivery method wherein releasing the valve frame from the delivery catheter is selected from the steps consisting of: (i) pulling the valve frame out of the delivery catheter using a rigid elongated pushing rod that is releasably connected to the distal side of the valve frame, wherein advancing the pushing rod away from the delivery catheter pulls the compressed valve frame out of the delivery catheter, or (ii) pushing the valve frame out of the delivery catheter using a rigid elongated pushing rod that is releasably connected to the proximal side of the valve frame, wherein advancing the pushing rod out of from the delivery catheter pushes the compressed valve frame out of the delivery catheter.

In another preferred embodiment of the invention, there is provided a delivery method comprising the additional step of anchoring one or more tissue anchors attached to the valve frame into native tissue.

In another preferred embodiment of the invention, there is provided a delivery method comprising the additional step of positioning a tension arm of the valve frame into the right ventricular outflow tract of the right ventricle.

In another preferred embodiment of the invention, there is provided a delivery method comprising the additional steps of positioning a lower tension arm of the valve frame into the right ventricular outflow tract of the right ventricle, and positioning an upper tension arm into a supra-annular position, and the upper tension arm providing a supra-annular downward force in the direction of the ventricle and lower tension arm providing a sub-annular upward force in the direction of the atrium.

In another preferred embodiment of the invention, there is provided a delivery method comprising the additional step of rotating the valve frame using a steerable catheter along an axis parallel to the plane of the valve annulus, wherein an upper tension arm mounted on the valve frame is conformationally pressure locked against supra-annular tissue, and wherein a lower tension arm mounted on the valve frame is conformationally pressure locked against sub-annular tissue.

In another preferred embodiment of the invention, there is provided a method for orthogonally loading an implantable prosthetic valve frame into a delivery catheter, the method comprising the step: loading an implantable prosthetic valve frame into a tapering fixture or funnel attached to a delivery catheter, wherein the valve frame comprises a tubular frame having a central lumen defined by an inner circumferential surface of the tubular frame, said tubular frame having an outer circumferential surface for engaging native annular tissue, wherein the tubular frame is compressible to a compressed orthogonal configuration for introduction into the body using a delivery catheter for implanting at a desired location in the body, said compressed orthogonal configuration having a horizontal long-axis oriented at an intersecting angle roughly perpendicular, e.g. 90 degrees, but ranging from between 45-135 degrees to a vertical axis of the central lumen, and expandable to an expanded configuration having a horizontal long-axis oriented at an intersecting angle roughly perpendicular, e.g. 90 degrees, but ranging from between 45-135 degrees to the vertical axis of the central lumen, wherein the horizontal long-axis of the compressed configuration of the tubular frame is substantially parallel to a length-wise cylindrical axis of the delivery catheter, wherein the tubular frame has a height of about 5-60 mm and a diameter of about 25-80 mm.

In another preferred embodiment of the invention, there is provided a loading method wherein the step of loading includes attaching a loading accessory to a valve sidewall, to a valve cuff, to a valve tension arm, or a combination thereof, wherein the loading accessory is pushing rod or a pulling wire, and wherein the tapering fixture or funnel has a compression element on an inner surface of the tapering fixture or funnel to facilitate compression, iris-ing, or spiraling of the uncompressed valve frame.

BRIEF DESCRIPTION OF THE SEVERAL VIEWS OF DRAWING

Figure 9:
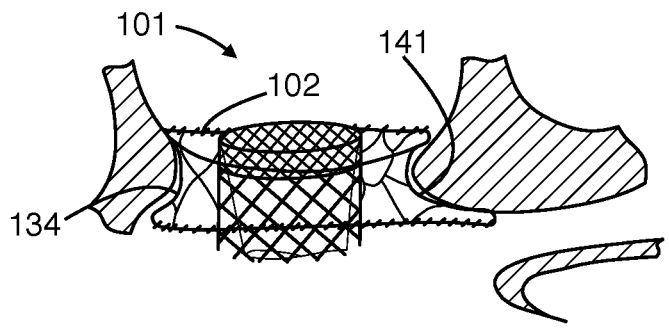

FIG. 9 is an illustration of a valve frame having a braid or laser-cut tubular frame and extended proximal tab or tension-arm engaging the tissue on the anterior side of the native annulus with the curved distal side-wall of the tubular frame sealing around the native annulus, and with the proximal side-wall tension-mounted into the posterior side of the native annulus, and a commercially available valve mounted within the lumen of the frame.

Figure 10:
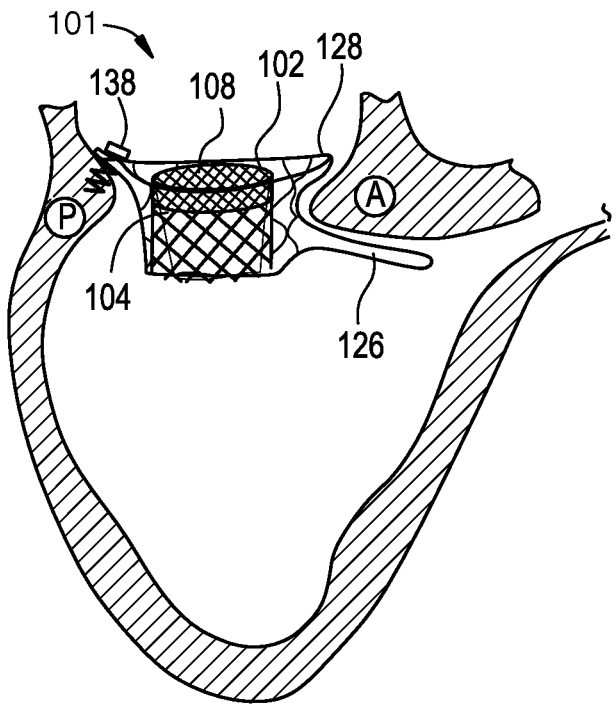

FIG. 10 is an illustration of a plan view of a valve frame prosthesis according to the present invention with a valve frame having a distal upper and lower tension arm mounted on, and anchored to, the anterior leaflet side of the native annulus, and having a mechanical anchor element, e.g. surgical tissue screw, anchored on a posterior or septal side of the native annulus. Independently deployed commercial valve is shown mounted within the aperture or lumen of the valve frame.

Figure 11:
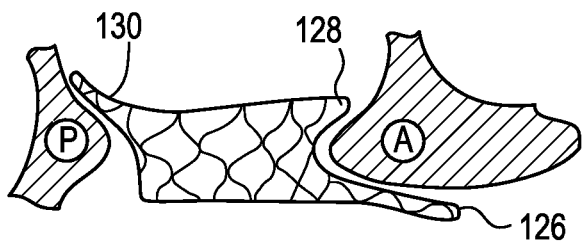

FIG. 11 is an illustration of a plan view of a valve frame prosthesis according to the present invention with a valve frame having a distal upper and lower tension arm mounted on, and anchored to, the anterior leaflet side of the native annulus, and having a mechanical anchor element, e.g. proximal sealing cuff, for anchoring on the posterior and septal side of the native annulus.

Figure 12:
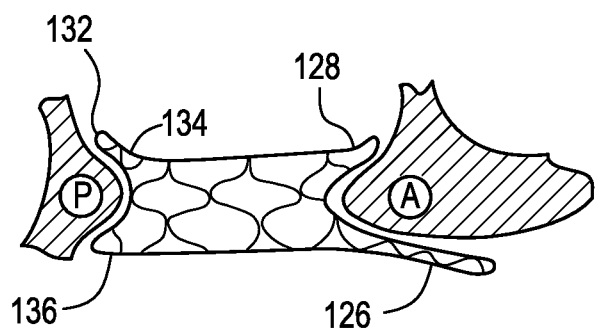

FIG. 12 is an illustration of a plan view of a valve frame prosthesis according to the present invention with a valve frame having a distal upper and lower tension arm mounted on, and anchored to, the anterior leaflet side of the native annulus, and having a mechanical anchor element, e.g. hourglass annular seal, for anchoring on the posterior and/or septal side of the native annulus.

Figure 13:
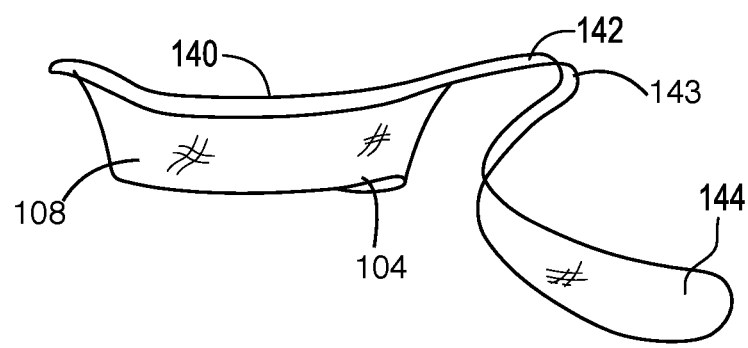

FIG. 13 is an illustration of a PLAN view of a low-profile, e.g. 10 mm in height, wire loop embodiment of the valve frame prosthesis having an annulus support loop and an upper and lower tension arm formed as a unitary or integral part, and covered with a biocompatible material.

Figure 14:
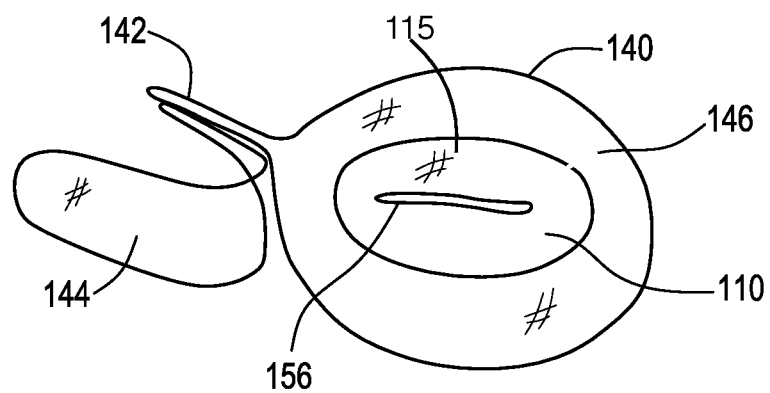

FIG. 14 is an illustration of a TOP view of a low-profile, e.g. 10 mm in height, wire loop embodiment of the valve frame prosthesis having an annulus support loop, an upper and lower tension arm formed as a unitary or integral part, an inner two-panel conical valve sleeve mounted therein, and said valve frame covered with a biocompatible material.

Figure 15:
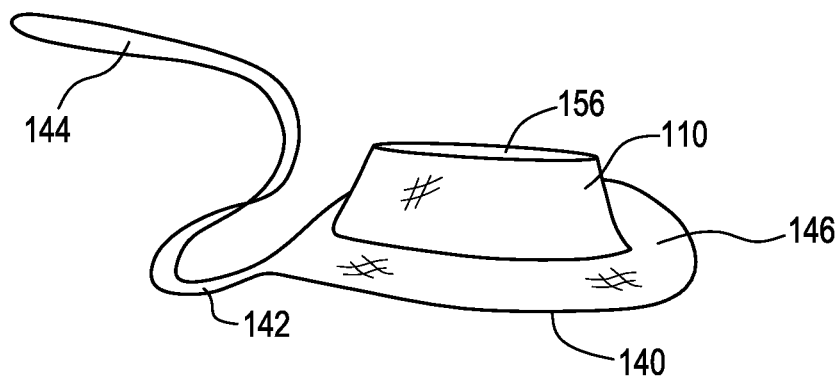

FIG. 15 is an illustration of a BOTTOM view of a low-profile, e.g. 10 mm in height, wire loop embodiment of the valve frame prosthesis having an annulus support loop, an upper and lower tension arm formed as a unitary or integral part, an inner two-panel conical valve sleeve mounted therein, and said valve frame covered with a biocompatible material.

Figure 16:
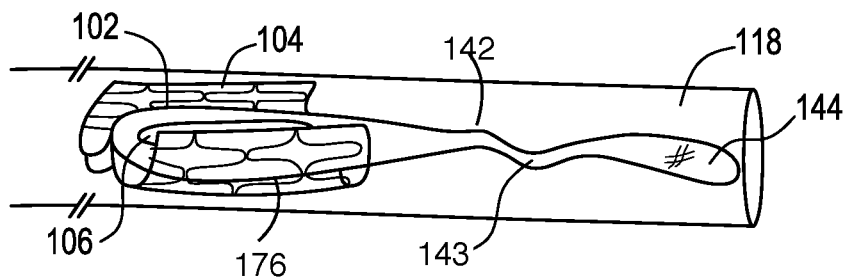

FIG. 16 is an illustration of a compressed and elongated wire loop embodiment of the valve frame prosthesis disposed within a delivery catheter and having an annulus support loop and an upper and lower tension arm formed as a unitary or integral part.

Figure 17:
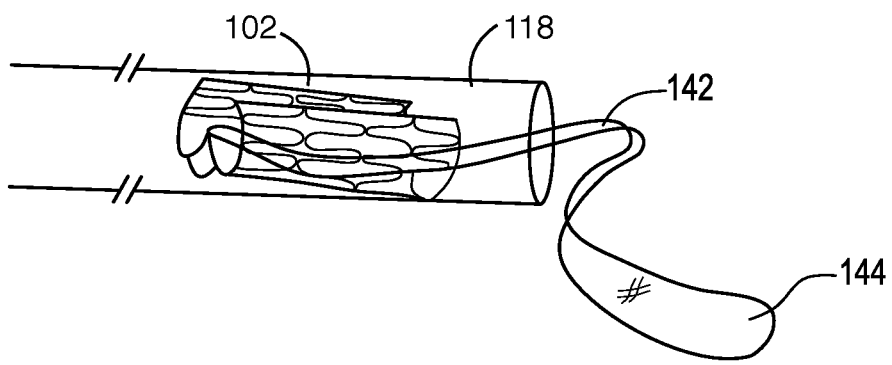

FIG. 17 is an illustration of a compressed and elongated wire loop embodiment of the valve frame prosthesis partially ejected, and partially disposed within, a delivery catheter and having an annulus support loop and an upper and lower tension arm formed as a unitary or integral part.

Figure 18:
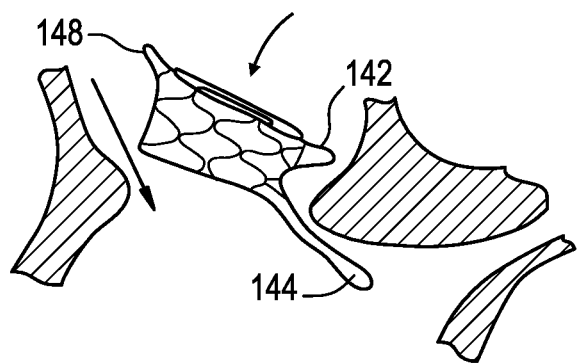

FIG. 18 is an illustration of a plan view of a valve frame prosthesis partially mounted within the valve annulus.

Figure 19:
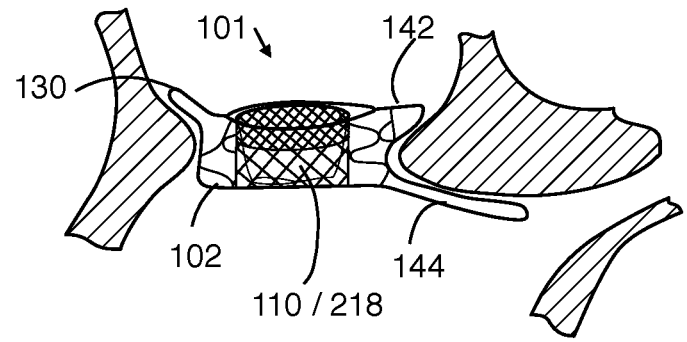

FIG. 19 is an illustration of a plan view of a valve frame prosthesis completely seated within the valve annulus. Independently deployed commercial valve is shown mounted within the aperture or lumen of the valve frame.

Figure 20:
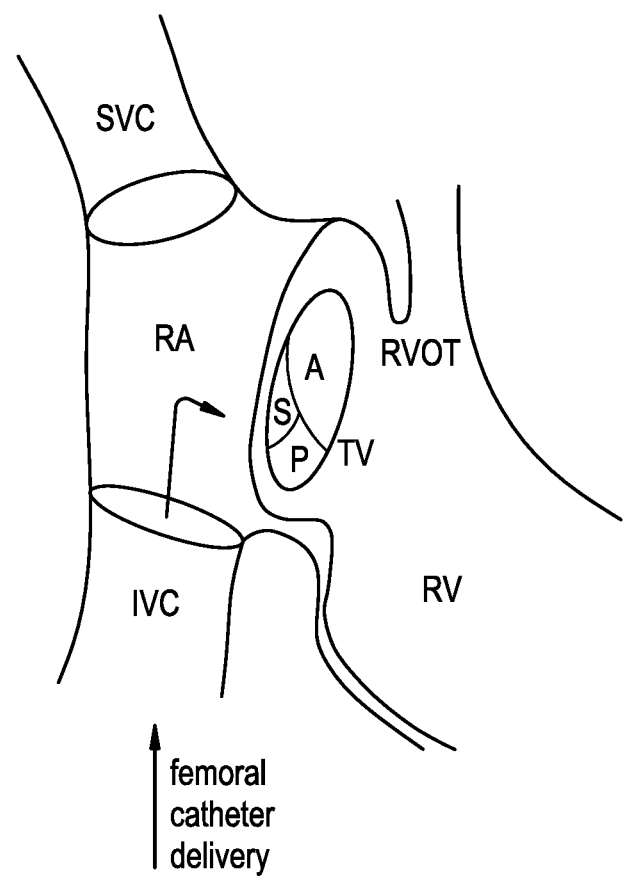

FIG. 20 is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet(S), the right ventricle (RV), and the right ventricular outflow tract (RVOT).

Figure 21:
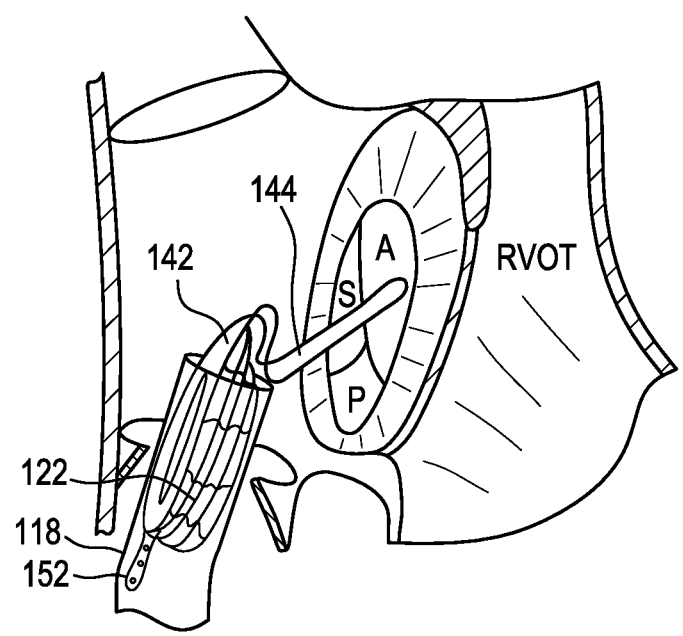

FIG. 21 is an illustration of a valve frame prosthesis having a wire-frame according to the present invention being delivered to tricuspid valve annulus.

Figure 22:
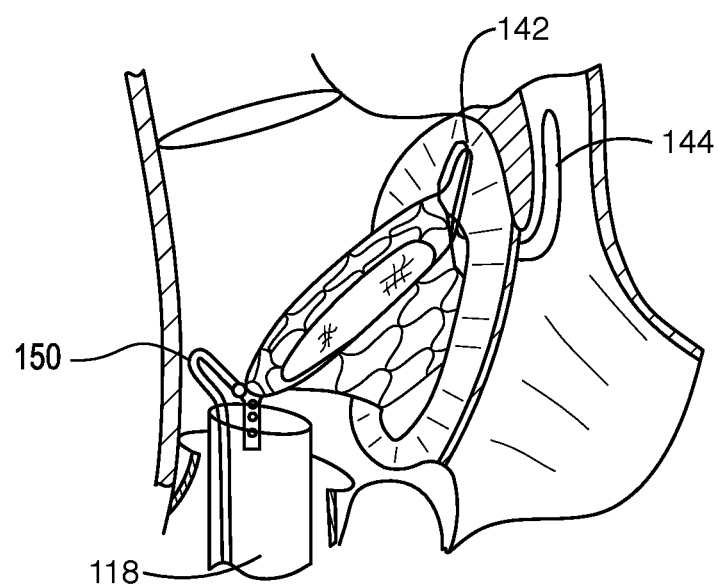

FIG. 22 is an illustration of a valve frame prosthesis having a wire-frame according to the present invention being delivered to tricuspid valve annulus.

Figure 23:
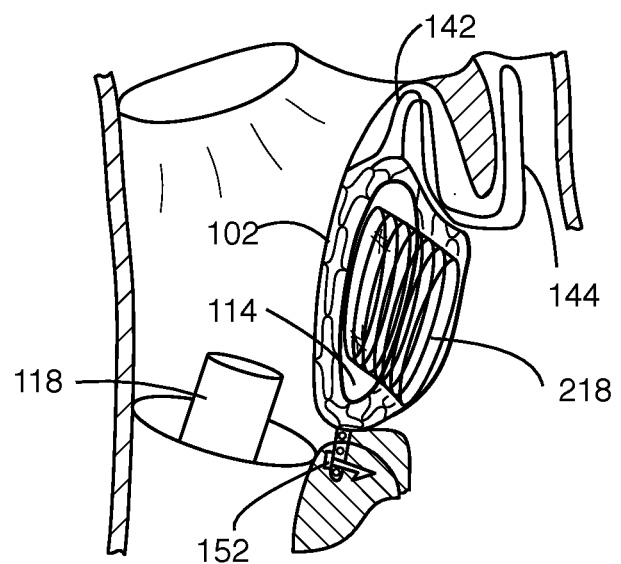

FIG. 23 is an illustration of a valve frame prosthesis having a wire-frame according to the present invention that has been delivered to tricuspid valve annulus. Independently deployed commercial valve is shown mounted within the aperture or lumen of the valve frame.

Figure 24:
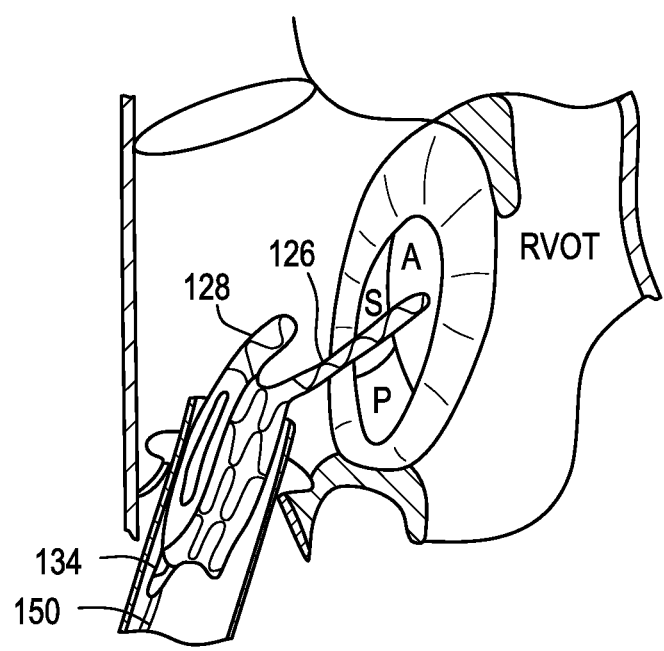

FIG. 24 is an illustration of a valve frame prosthesis having a braided/laser cut-frame according to the present invention being delivered to tricuspid valve annulus.

Figure 25:
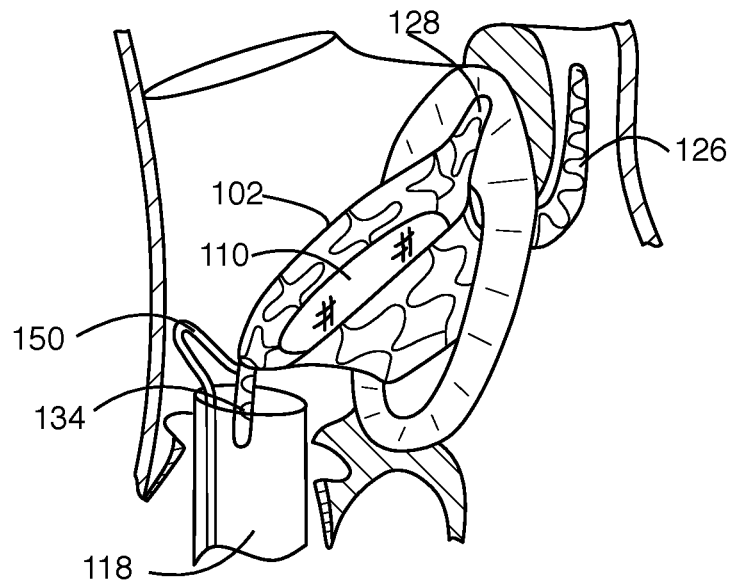

FIG. 25 is an illustration of a valve frame prosthesis having a braided/laser cut-frame according to the present invention being delivered to tricuspid valve annulus.

Figure 26:
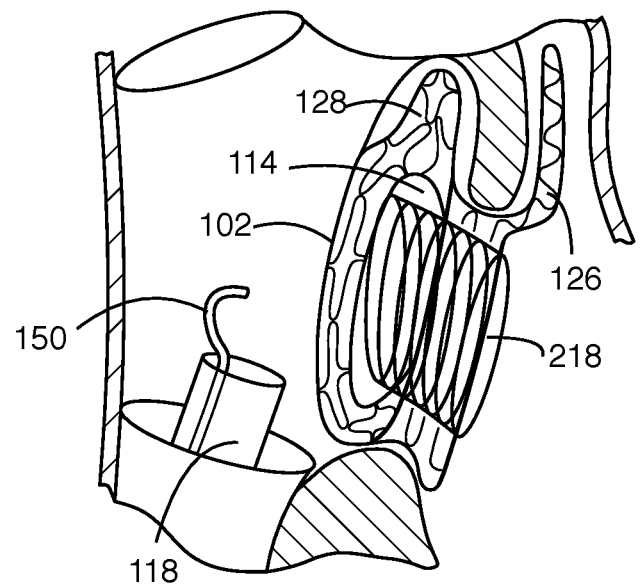

FIG. 26 is an illustration of a valve frame prosthesis having a braided/laser cut-frame according to the present invention that has been delivered to tricuspid valve annulus. Independently deployed commercial valve is shown mounted within the aperture or lumen of the valve frame.

Figure 27:
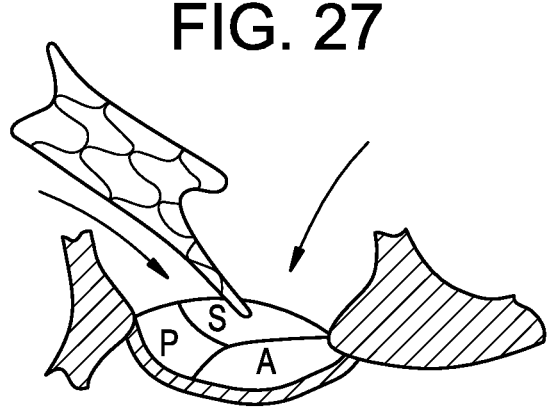

FIG. 27 is an illustration of a valve frame prosthesis according to the present invention being delivered to tricuspid valve annulus and shows step 1 in a valve assessment process.

Figure 28:
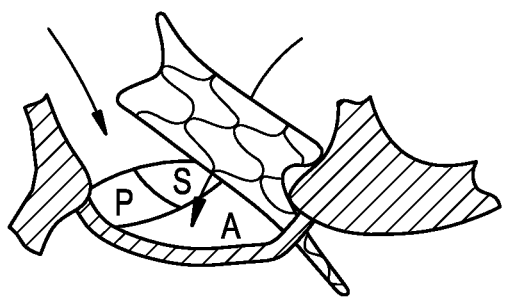

FIG. 28 is an illustration of a valve frame prosthesis according to the present invention being delivered to tricuspid valve annulus, and shows Step 2 in a valve assessment process.

Figure 29:
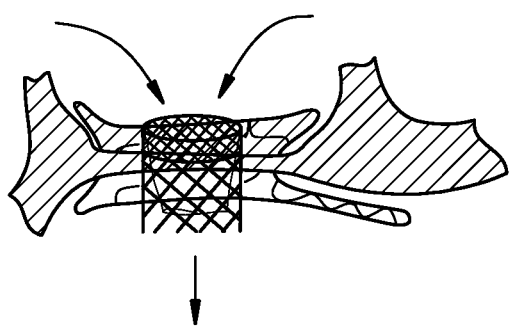

FIG. 29 is an illustration of a valve frame prosthesis according to the present invention that has been delivered to tricuspid valve annulus, and shows Step 3 in a valve assessment process, with independently deployed commercial valve shown mounted within the aperture or lumen of the valve frame.

Figure 30:
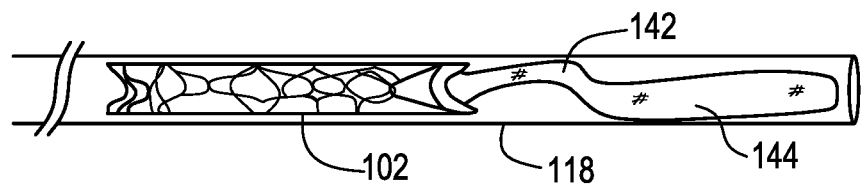

FIG. 30 is an illustration of a wire-frame embodiment of a valve frame prosthesis according to the present invention in a compressed, intra-catheter phase.

Figure 31:
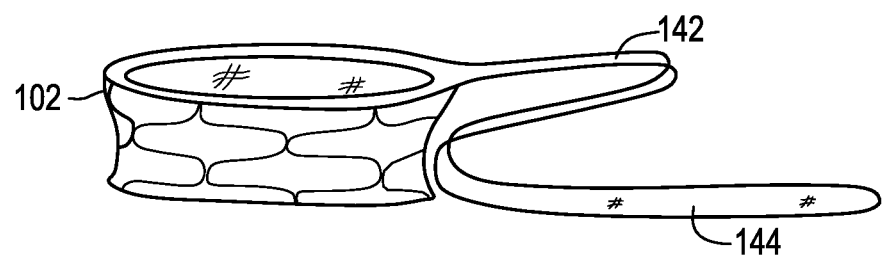

FIG. 31 is an illustration of a profile, or plan, view of a wire-frame embodiment of the valve frame prosthesis according to the present invention in a un-compressed, post-catheter-ejection phase.

Figure 32:
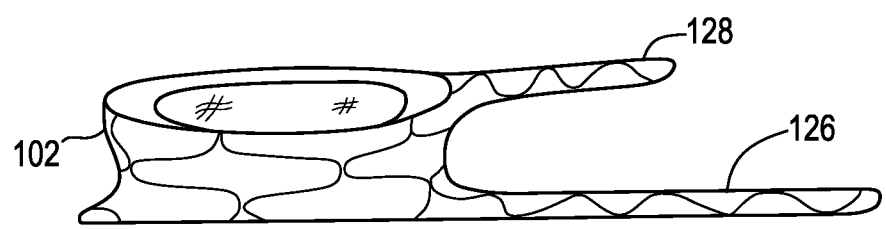

FIG. 32 is an illustration of a profile, or plan, view of a braided or laser-cut frame embodiment of the valve frame prosthesis according to the present invention in a un-compressed, post-catheter-ejection phase.

FIG. 33 is an illustration of a TOP view of a valve frame prosthesis according to the present invention having covered wire loops for the upper tension arm(s). Tri-leaflet flow control structure from an aperture mounted valve are shown.

FIG. 34 is an illustration of a PLAN view of a valve frame prosthesis according to the present invention having a wire loop construction for the upper and lower tension arms.

FIG. 35 is an illustration of a CUT-AWAY PLAN view of a valve frame prosthesis according to the present invention, and shows the independently deployed commercial valve mounted within the inner space/aperture/lumen defined by the inner circumferential surface of the tubular frame.

FIG. 36 is an illustration of a BOTTOM view of a valve frame prosthesis according to the present invention having covered wire loops for the lower tension arm. Tri-leaflet structures from an aperture mounted valve are shown.

Figure 37:
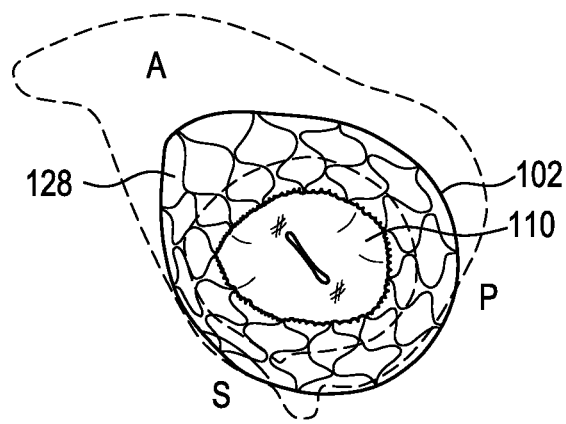

FIG. 37 is an illustration of a TOP view of a valve frame prosthesis according to the present invention having braid or laser-cut wire frame for the upper tension arm(s). Bi-leaflet flow control structure from an aperture mounted valve are shown.

Figure 38:
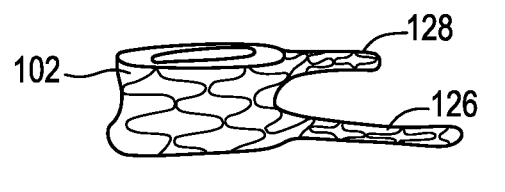

FIG. 38 is an illustration of a PLAN view of a valve frame prosthesis according to the present invention having braid or laser-cut wire frame construction for the upper and lower tension arms.

Figure 39:
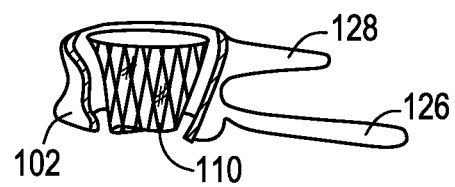

FIG. 39 is an illustration of a CUT-AWAY PLAN view of a braid or laser-cut embodiment of the valve frame prosthesis according to the present invention, and shows the independently deployed commercial valve mounted within the inner space defined by the inner circumferential surface of the tubular frame.

Figure 40:
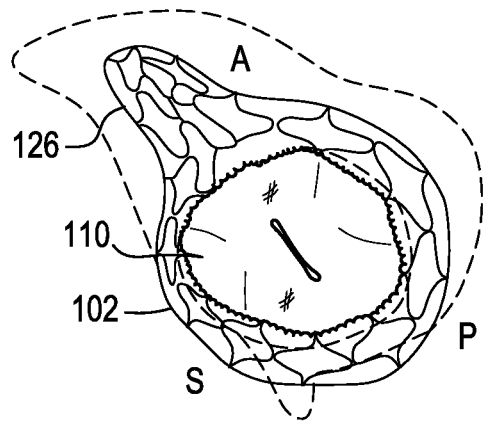

FIG. 40 is an illustration of a BOTTOM view of a valve frame prosthesis according to the present invention having braid or laser-cut wire frame for the lower tension arm.

Figure 41:
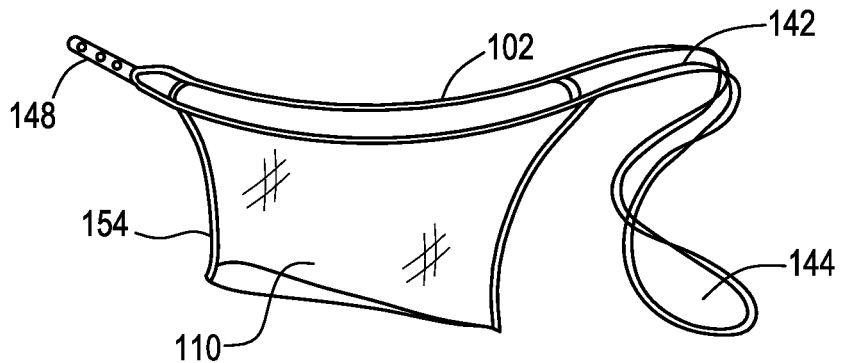

FIG. 41 is an illustration of a valve frame prosthesis according to the present invention having a wire loop construction for the tubular frame, with two vertical support posts extending down the edge on opposing sides of the valve sleeve. During compression into the delivery catheter, the posts are engineered to fold horizontally during compression, and to elastically unfold during ejection to deploy the valve.

Figure 42:
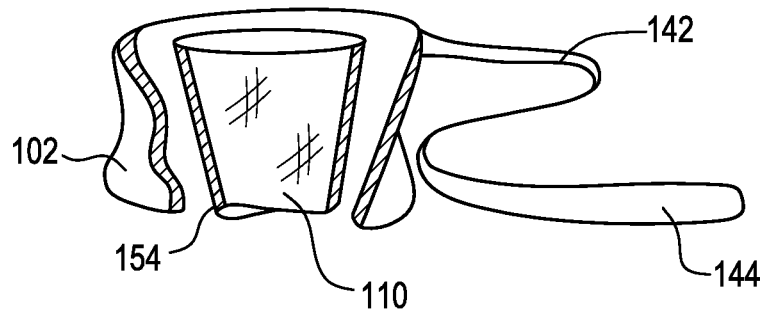

FIG. 42 is an illustration of a CUT-AWAY PLAN view of a valve frame prosthesis according to the present invention, and shows a independently deployed commercial valve mounted within the inner space defined by the tubular frame.

Figure 43:
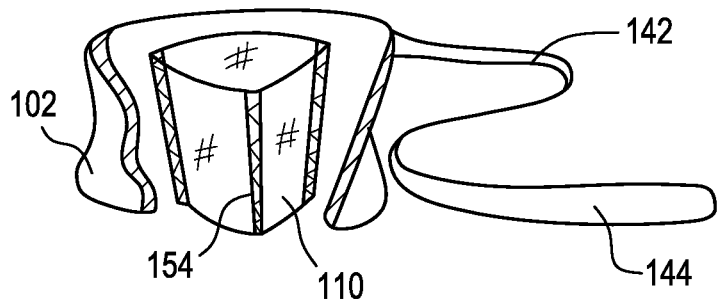

FIG. 43 is an illustration of a CUT-AWAY PLAN view of a valve frame prosthesis according to the present invention, and shows a independently deployed commercial valve mounted within the inner space defined by the tubular frame.

Figure 44:
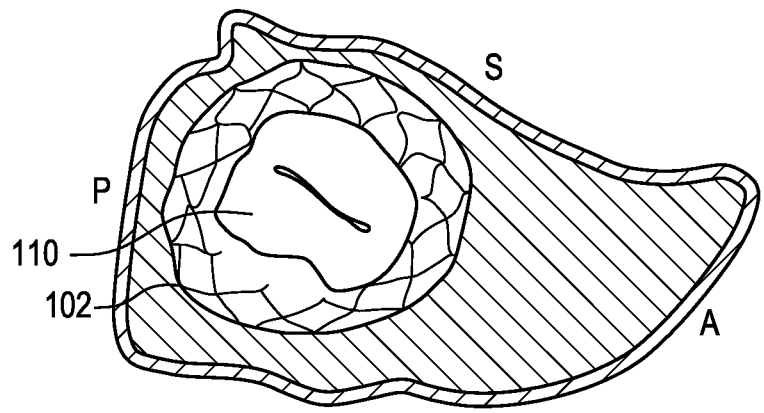

FIG. 44 is an illustration of a TOP view of a valve frame according to the present invention having braid or laser-cut wire frame and shown mounted within a cross-sectional view of the atrial floor at the annulus.

Figure 45:
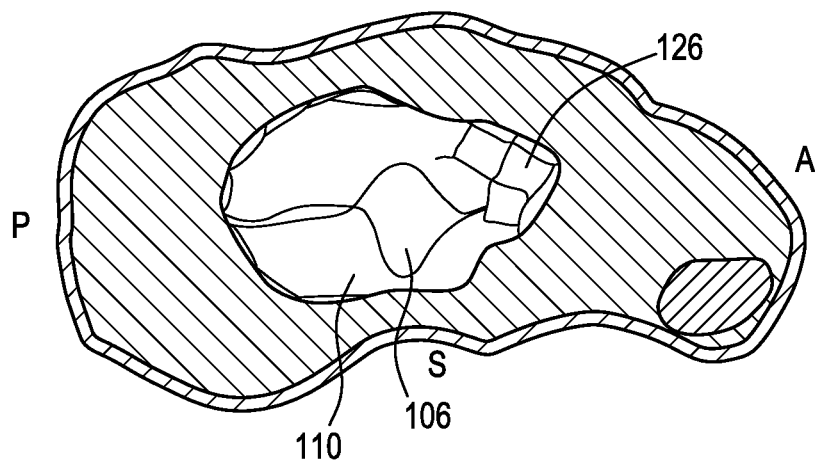

FIG. 45 is an illustration of a BOTTOM view of a valve frame according to the present invention having braid or laser-cut wire frame for a lower tension arm and shown mounted within a cross-sectional view of the ventricular ceiling at the annulus.

Figure 46:
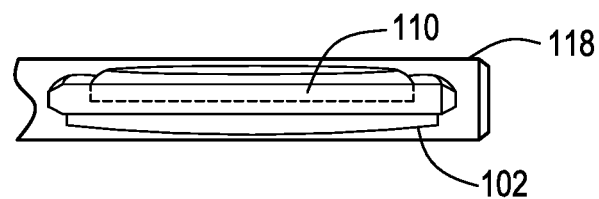

FIG. 46 is an illustration of a PLAN view of an embodiment of the valve frame shown in a compressed configuration within a delivery catheter.

Figure 47:
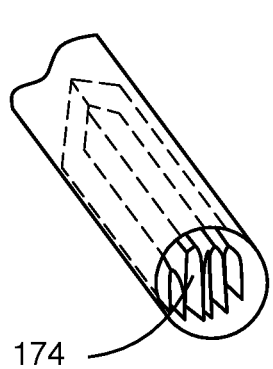

FIG. 47 is an illustration of a cross-sectional view of one embodiment of a compressed valve frame within a delivery catheter.

Figure 48:
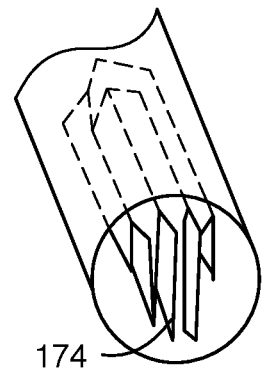

FIG. 48 is an illustration of a cross-sectional view of another embodiment of a compressed valve frame within a delivery catheter.

Figure 49:
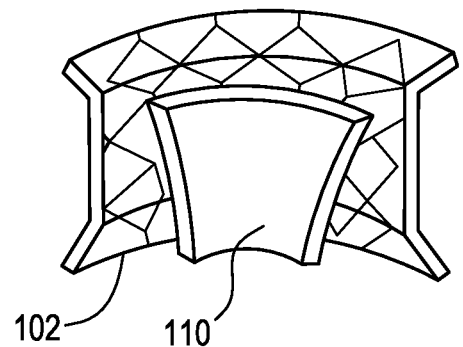

FIG. 49 is an illustration of a cross-sectional view of one embodiment of the prosthetic valve frame.

Figure 50A:
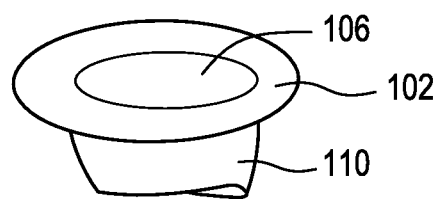
Figure 50B:
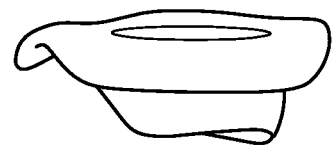
Figure 50C:

FIG. 50(a)-(b)-(c) is an illustration of a sequence of a low-profile valve frame being rolled into a configuration for placement within a delivery catheter.

Figure 51:
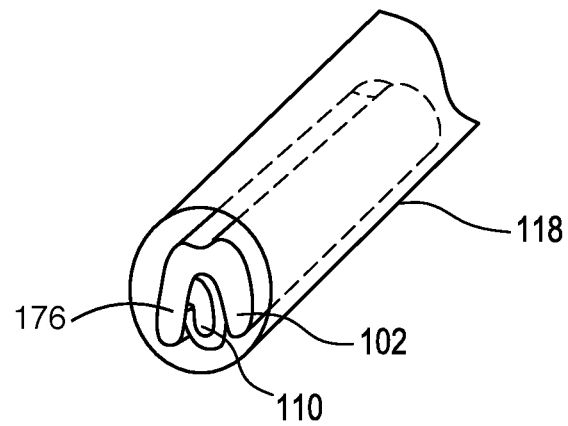

FIG. 51 is an illustration of an END-VIEW of a low-profile valve frame that has been longitudinally rolled and loaded within a delivery catheter.

Figure 52:
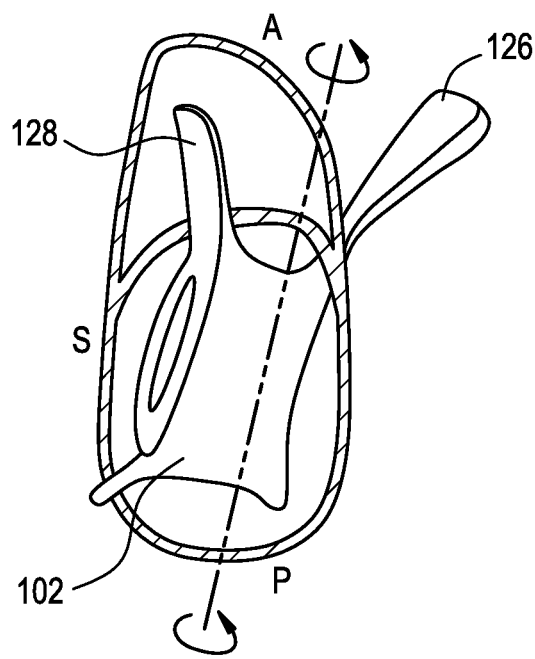

FIG. 52 is an illustration of a rotational lock embodiment of the present invention where the valve frame is delivered to the native annulus with an off-set sub-annular tension arm/tab positioned below the native annulus, and an off-set supra-annular tension arm/tab positioned above the native annulus, while the tubular frame is partially rolled off-set from the annular plane along a longitudinal axis.

Figure 53:
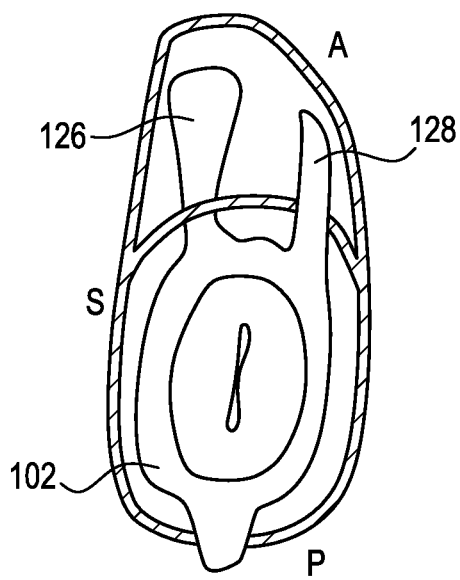

FIG. 53 is an illustration of a rotational lock embodiment of the present invention where the valve frame is delivered to the native annulus with an off-set sub-annular tension arm/tab positioned below the native annulus, and an off-set supra-annular tension arm/tab positioned above the native annulus, while the tubular frame is rolled into functional position parallel to the annular plane.

Figure 54:
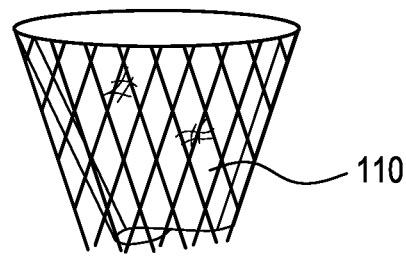

FIG. 54 is an illustration of a independently deployed balloon expandable commercial valve.

Figure 55:
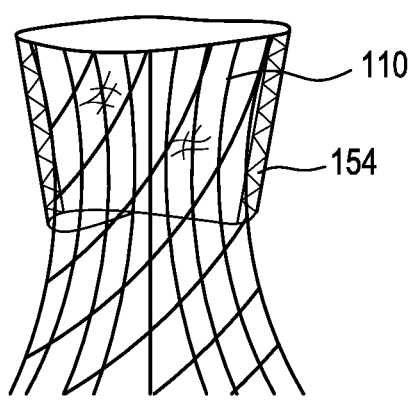

FIG. 55 is an illustration of a self-expanding independently deployed commercial valve.

Figure 56:
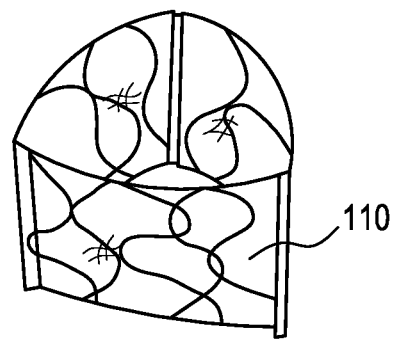

FIG. 56 is an illustration of a three-panel embodiment of a self-expanding independently deployed valve.

Figure 57:
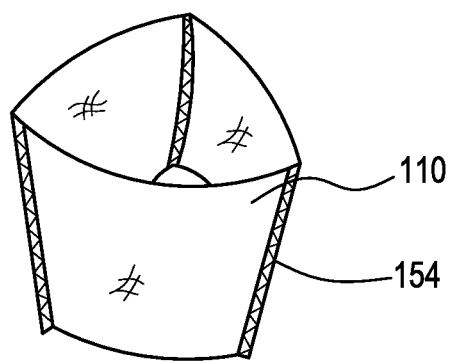

FIG. 57 is an illustration of a three-panel embodiment of a independently deployed valve having three rigid support posts.

Figure 58:
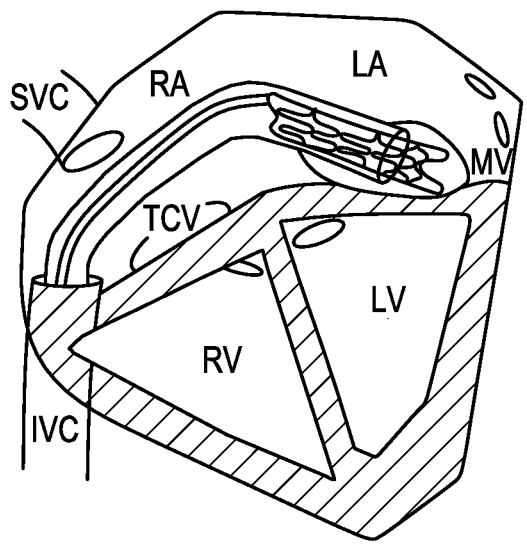

FIG. 58 is an illustration of the trans-septal (femoral-IVC) delivery of a low-profile, e.g. 8-20 mm, side-loaded prosthetic MITRAL valve frame shown partially housed within the delivery catheter, and partially ejected for deployment into the native mitral annulus.

Figure 59:
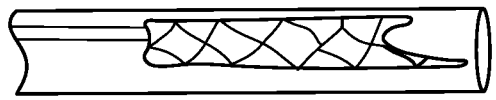

FIG. 59 is an illustration of a low-profile, e.g. 8-20 mm, side-loaded prosthetic MITRAL valve frame shown housed within the delivery catheter.

Figure 60:
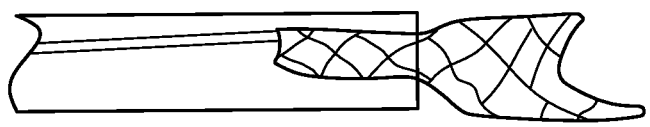

FIG. 60 is an illustration of a low-profile, e.g. 8-20 mm, side-loaded prosthetic MITRAL valve frame shown partially housed within a delivery catheter and partially laterally ejected from the delivery catheter and positioned for deployment against the anterior side of the native mitral annulus.

Figure 61:
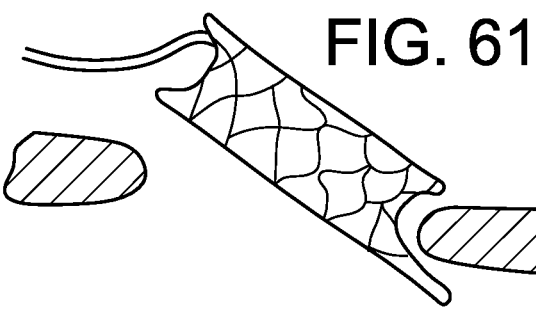

FIG. 61 is an illustration of a low-profile, e.g. 8-20 mm, side-loaded prosthetic MITRAL valve frame shown ejected from the delivery catheter and positioned against the anterior side of the native mitral annulus.

Figure 62:

FIG. 62 is an illustration of a side or plan view of a low-profile, e.g. 8-20 mm, side-loaded prosthetic valve frame shown deployed into the native MITRAL annulus.

Figure 63:
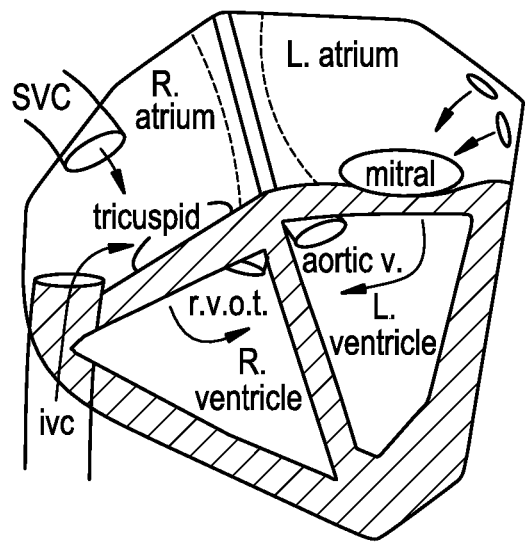

FIG. 63 is an illustration of the heart and shows an approximate location of the valves, the left and right atrium, the left and right ventricles, and the blood vessels that enter and exit the chambers of the heart.

Figure 64:
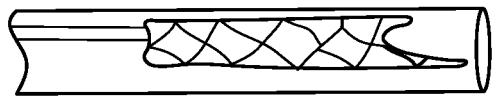

FIG. 64 is an illustration of a low-profile, e.g. 8-20 mm, side-loaded valve frame shown housed within the delivery catheter.

Figure 65:
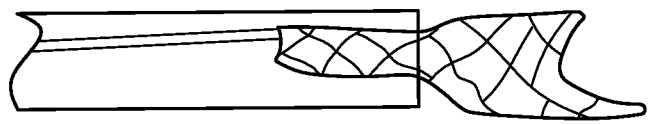

FIG. 65 is an illustration of a low-profile, e.g. 8-20 mm, side-loaded valve frame shown partially housed within a delivery catheter and partially laterally ejected from the delivery catheter and positioned for deployment against the anterior side of the native annulus.

Figure 66:
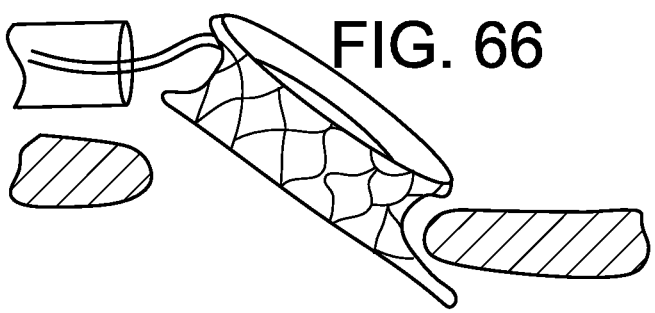

FIG. 66 is an illustration of a low-profile, e.g. 8-20 mm, side-loaded valve frame shown ejected from the delivery catheter and positioned against the anterior side of the native annulus.

Figure 67:
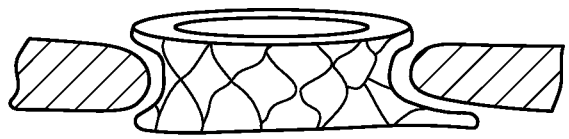

FIG. 67 is an illustration of a side or plan view of a low-profile, e.g. 8-20 mm, side-loaded valve frame shown deployed into the native annulus of a heart valve.

Figure 68:
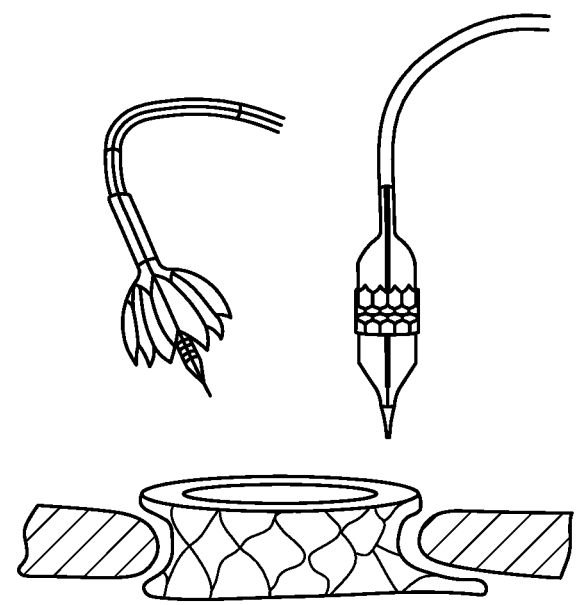

FIG. 68 is an illustration of a side view of two types of deliverable valves, the first is a self-expanding transcatheter valve, and the second is a commercially-approved transcatheter balloon-expandable prosthetic valve being vertically deployed into the central lumen of the already (laterally, horizontally, orthogonally) deployed valve frame.

Figure 69:
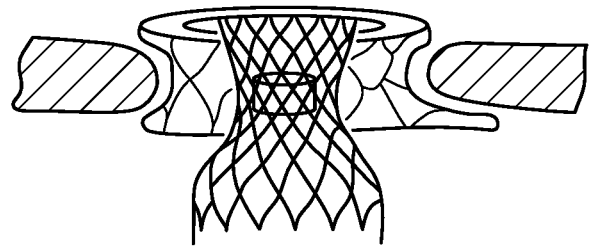

FIG. 69 is an illustration of a side view of a commercially-approved transcatheter self-expandable prosthetic valve mounted within the central lumen of the already (laterally, horizontally, orthogonally) deployed valve frame.

Figure 70:
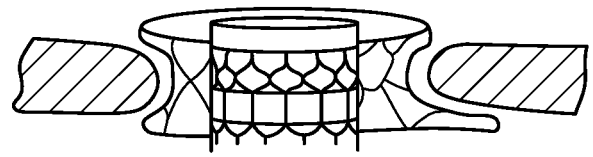

FIG. 70 is an illustration of a side view of a commercially-approved transcatheter balloon-expandable prosthetic valve mounted within the central lumen of the already (laterally, horizontally, orthogonally) deployed valve frame.

DETAILED DESCRIPTION OF THE INVENTION

The invention is directed to a transcatheter heart valve replacement that is a low profile, orthogonally delivered implantable prosthetic valve having an ring-shaped tubular frame, an inner 2- or 3-panel sleeve, an elongated sub-annular tension arm extending into the right ventricular outflow tract, and one or more anchor elements.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Orthogonal

In the description and claims herein, the term "orthogonal" is used to describe that the valves of the present invention are compressed and delivered at a roughly 90 degree angle compared to traditional transcatheter heart valves. Traditional valves have a central cylinder axis that is parallel to the length-wise axis of the delivery catheter and are deployed from the end of the delivery catheter in a manner akin to pushing a closed umbrella out of a sleeve. The valves of the present invention are compressed and delivered in a sideways manner. Traditional valves can only be expanded as large as what the internal diameter of the delivery catheter will allow. Efforts to increase the expanded diameter of traditional valves have run into the problems of trying to compress too much material and structure into too little space. Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic valve where the blood is flowing, eg. from one part of the body or chamber of the heart to another downstream part of the body or chamber of the heart, such as from an atrium to a ventricle through a native annulus. The intersecting angle may also include 45-135 degrees from normal, i.e. the central axis of the native annulus or the central axis (parallel to blood flow) of the deployed valve.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

Tubular Frame

In the description and claims herein, the term "tubular frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve, but does not include such a leaflet structure or flow control structure unless further stated.

Prosthetic Valve Frame

In the description and claims herein, the term "valve frame" or "prosthetic valve frame" or "valve-in-valve" refers to a three-dimensional structural component, usually tubular, cylindrical, or oval or ring-shaped, and that is seated within a native valve annulus and is used as a mounting element for a commercially available valve such as a Sapien®, Sapien 3®, and Sapien XT® from Edwards Lifesciences, the Inspiris Resilia aortic valve from Edwards Lifesciences, the Masters HP 15 mm valve from Abbott, Lotus Edge valve from Boston Scientific, the Crown PRT leaflet structure from Livanova/Sorin, the Carbomedics family of valves from Sorin, or other flow control component, or a flexible reciprocating sleeve or sleeve-valve.

Valve Frame Structure

The term "frame" as used in the description and claims herein, refers to a flexible structure that is mounted within the lumen of a ring or conduit of native tissue, and that surrounds, encircles, or encloses, in part or wholly, an opening or space. As used herein, a "frame" functions to support a leaflet structure or other flow control structure. The valve frame can be a tube, ring, or cylindrical or conical tube, made from a durable, biocompatible structural material such as Nitinol or similar alloy, wherein the valve frame is formed by manufacturing the structural material as a braided wire frame, a laser-cut wire frame, or a wire loop. The valve frame is about 5-60 mm in height, has an outer diameter dimension, R, of 30-80 mm, and an inner diameter dimension of 31-79 mm, accounting for the thickness of the wire material itself. As stated, the valve frame can have a side-profile of a tubular shape, a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the valve frame used for mounting a prosthetic valve deployed in the tricuspid annulus, and may have a complex shape determined by the anatomical structures where the valve frame is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic valve may start in a roughly tubular configuration, and be heat-shaped to provide an upper atrial cuff or flange for atrial sealing and a lower trans-annular tubular section having an hourglass cross-section for about 60-80% of the circumference to conform to the native annulus along the posterior and anterior annular segments while remaining substantially vertically flat along 20-40% of the annular circumference to conform to the septal annular segment.

Valve Frame Covering

The valve frame is optionally internally or externally covered, partially or completely, with a biocompatible material such as pericardium. The valve frame may also be optionally externally covered, partially or completely, with a second biocompatible material such as polyester or Dacron®).

Valve Frame Purpose

The valve frame has a central axial lumen where a prosthetic valve or flow-control structure, such as a reciprocating compressible sleeve, is mounted across the diameter of the lumen. The valve frame has an outer circumferential surface for engaging native annular tissue that is also tensioned against the inner aspect of the native annulus and provides structural patency to a weakened native annular ring.

Valve Frame Optional Collars

The valve frame may optionally have a separate atrial collar attached to the upper (atrial) edge of the frame, for deploying on the atrial floor, that is used to direct blood from the atrium into the sleeve and to seal against blood leakage around the valve frame. The valve frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Valve Frame Delivery

The valve frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic valves having either a single atrial collar, a single ventricular collar, or having no additional collar structure.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a tubular frame, to function as a prosthetic valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of –, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term "valve prosthesis" or "prosthetic valve" refers to a combination of a frame and a leaflet or flow control structure, and encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bio-prostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Frame Material

Preferably, the frame is made from superelastic metal wire, such as Nitinol™ wire or other similarly functioning material. The material may be used for the frame/stent, for the collar, and/or for anchors. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers. It is contemplated that the frame may be constructed as a braid, wire, or laser cut wire frame. Such materials are available from any number of commercial manufacturers, such as Pulse Systems. Laser cut wire frames are preferably made from Nickel-Titanium (Nitinol™), but also without limitation made from stainless steel, cobalt chromium, titanium, and other functionally equivalent metals and alloys, or Pulse Systems braided frame that is shape-set by heat treating on a fixture or mandrel.

One key aspect of the frame design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required compression features.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is placed on a mold of the desired shape, heated to the Martensitic temperature and quenched. The treatment of the wire frame in this manner will form a device that has shape memory properties and will readily revert to the memory shape at the calibrated temperature.

Braided Wire

A frame can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Tethers—The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, a prosthetic valve frame may include an atrial collar, a ventricular collar, or both.

Tube and/or Cover Material—Biological Tissue

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example

One preferred embodiment of an orthogonally delivered transcatheter prosthetic valve frame has a tubular frame, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve is substantially parallel to a length-wise cylindrical axis of the delivery catheter, wherein the valve has a height of about 5-60 mm and a diameter of about 25-80 mm.

This heart valve frame can be delivered to the heart using the inferior vena cava (IVC/femoral transcatheter delivery pathway compressed within a catheter, and expelled from the catheter to be deployed without open heart surgery.

Example

In another preferred embodiment of a transcatheter valve frame, comprises: a cylindrical tubular frame having a height of about 5-60 mm and an outer diameter of about 25-80 mm, said tubular frame comprised of a braid, wire, or laser-cut wire frame having a substantially circular central aperture, said tubular frame partially covered with a biocompatible material; an upper tension arm attached to a distal upper edge of the tubular frame, the upper tension arm comprised of stent, segment of tubular frame, wire loop or wire frame extending from about 10-30 mm away from the tubular frame; a lower tension arm extending from a distal side of the tubular frame, the lower tension arm comprised of stent, segment of tubular frame, wire loop or wire frame extending from about 10-40 mm away from the tubular frame; and at least one tissue anchor to connect the tubular frame to native tissue.

Example

In a preferred embodiment of the invention, there is also provided a method for orthogonal delivery of implantable prosthetic valve frame to a desired location in the body, the method comprising the steps: (i) advancing a delivery catheter to the desired location in the body and delivering an expandable prosthetic valve frame to the desired location in the body by releasing the valve frame from the delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a length-wise cylindrical axis of the delivery catheter, wherein the valve frame has a height of about 5-60 mm and a diameter of about 25-80 mm.

Example

In a preferred embodiment of the invention, there is also provided a method for orthogonally loading an implantable prosthetic valve frame into a delivery catheter, the method comprising the steps: loading an implantable prosthetic valve frame sideways into a tapering fixture or funnel attached to a delivery catheter, wherein the valve frame is compressible to a compressed configuration for introduction into the body using a delivery catheter for implanting at a desired location in the body, said compressed configuration having a long-axis oriented at an intersecting angle of between 45-135 degrees to the central, cylindrical axis of the native annulus, and expandable to an expanded configuration having a long-axis oriented at an intersecting angle of between 45-135 degrees to the central, cylindrical axis of the native annulus, wherein the long-axis of the compressed configuration of the valve frame is substantially parallel to a length-wise cylindrical axis of the delivery catheter, wherein the valve frame has a height of about 5-60 mm and a diameter of about 25-80 mm.

Example

The transcatheter prosthetic heart valve may be percutaneously delivered using a transcatheter process via the femoral through the inferior vena cava (IVC), superior vena cava (SVC), jugular vein, brachial vein, sub-xyphoid, intercostal access across the chest wall, and trans-septal through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in a preferred embodiment the valve frame self-expands upon release from the catheter since it is constructed in part from shape-memory material, such as Nitinol®, a nickel-titanium alloy used in biomedical implants.

In another embodiment, the valve frame may be constructed of materials that requires balloon-expansion after the capsule has been ejected from the catheter into the atrium.

The atrial collar/frame is expanded to their functional diameter, and deployed into the native annulus, providing a radial tensioning force to secure the valve frame. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning.

DRAWINGS

Figure 1:
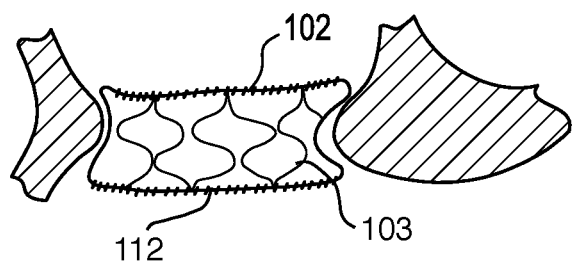
FIG. 1 is an illustration of a low-profile, e.g. 8-20 mm, side-loaded prosthetic valve frame shown deployed into the native annulus.

Referring now to the drawings, FIG. 1 is an illustration of a low-profile, e.g. 8-20 mm, side-loaded prosthetic valve frame 102 shown deployed into the native annulus. FIG. 1 shows that low-profile, side-loaded valve frames can be delivered and traditionally anchored without the need for shaped, tension arms. FIG. 1 also shows compressible wire cells 103 and suture supports 112.

Figure 2:
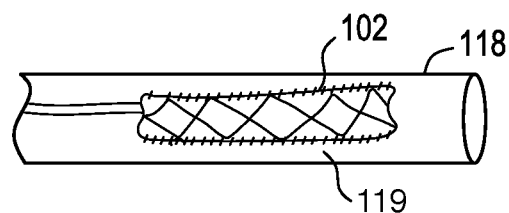
FIG. 2 is an illustration of a low-profile, e.g. 8-20 mm, side-loaded prosthetic valve frame shown compressed or housed within the delivery catheter.

FIG. 2 is an illustration of a low-profile, e.g. 8-20 mm, side-loaded prosthetic valve frame having frame 102 shown compressed or housed within the lumen 119 of the delivery catheter 118.

Figure 3:
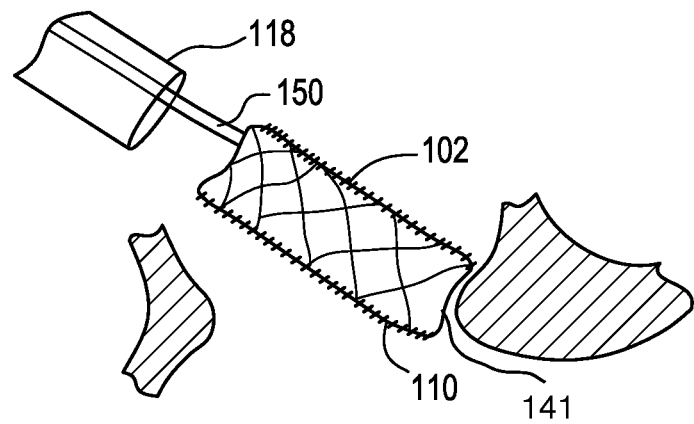
FIG. 3 is an illustration of a low-profile, e.g. 8-20 mm, side-loaded prosthetic valve frame shown ejected from the delivery catheter and positioned against the anterior side of the native annulus.

FIG. 3 is an illustration of a low-profile, e.g. 8-20 mm, side-loaded prosthetic valve frame 102 shown ejected from the delivery catheter 118 and positioned with sidewall 141 against the anterior side of the native annulus. While the valve is held at this oblique angle by secondary catheter 150, valve frame function and patient condition are assessed, and if appropriate the valve is then completely deployed within the native annulus, and anchored using traditional anchoring elements.

Figure 4:
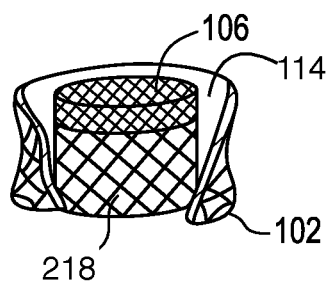
FIG. 4 is an illustration of a open cross-section view of a low-profile, side-loaded prosthetic valve frame and shows a commercially available valve mounted within the lumen of the frame.

FIG. 4 is an illustration of a open cross-section view of a low-profile, side-loaded prosthetic valve frame 102 and shows an example of a commercially available valve 218 mounted within the inner surface 114 of frame 102.

Figure 5:
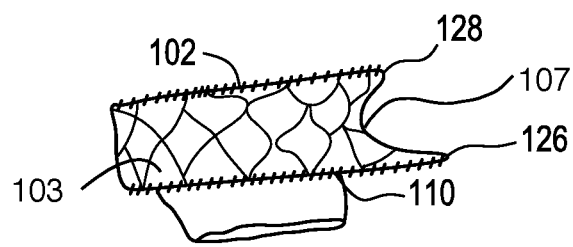
FIG. 5 is an illustration of a valve frame according to the present invention having a braid or laser-cut construction for the tubular frame, with an extended tab or tension arm that extends away from the tubular frame.

FIG. 5 is an illustration of a low-profile, side-loaded valve frame 102 according to the present invention having a braid or laser-cut construction of compressible wire cells 103 for the tubular frame 102. FIG. 5 shows a longer lower tension arm 126 for extending sub-annularly towards the right ventricular outflow tract RVOT, and connected by a curved annular distal channel 107 in the frame 102 to a shorter upper tension arm 128 for extending over the atrial floor. FIG. 5 shows an elongated two (2) panel valve sleeve 110 that extends into the sub-annular leaflet space. The tubular frame 102 shown in FIG. 5 is about 10 mm in height and the valve sleeve 110 extends about 10 mm below the bottom of the tubular frame, resulting in a valve 20 mm in total height.

Figure 6:
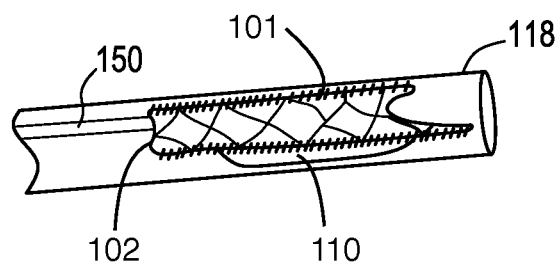
FIG. 6 is an illustration of a valve frame having a braid or laser-cut tubular frame and extended valve sleeve compressed within a delivery catheter.

FIG. 6 is an illustration of a low-profile, side-loaded valve frame prosthesis 101 having a braid or laser-cut tubular frame 102 and extended valve sleeve 110 compressed within a delivery catheter 118. FIG. 6 shows the valve attached to a secondary steerable catheter 150 for ejecting, positioning, and anchoring the valve frame. The secondary catheter 150 can also be used to retrieve a failed deployment of a valve frame.

Figure 7:
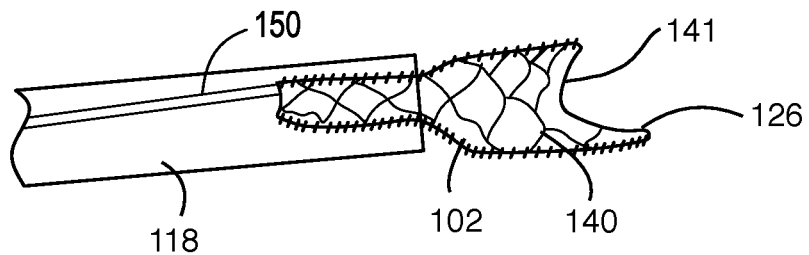
FIG. 7 is an illustration of a valve frame having a braid or laser-cut tubular frame and extended valve sleeve shown partially compressed within a delivery catheter, and partially ejected from the delivery catheter.

FIG. 7 is an illustration of a valve frame 102 having a braid or laser-cut tubular frame 140 shown partially compressed within a delivery catheter 118, and partially ejected from the delivery catheter. FIG. 7 shows that while the valve frame 102 is still compressed the lower tension arm 126 can be manipulated through the native leaflets and chordae tendinae to find a stable anterior-side lodgment for the distal side 141 of the valve frame 102.

Figure 8:
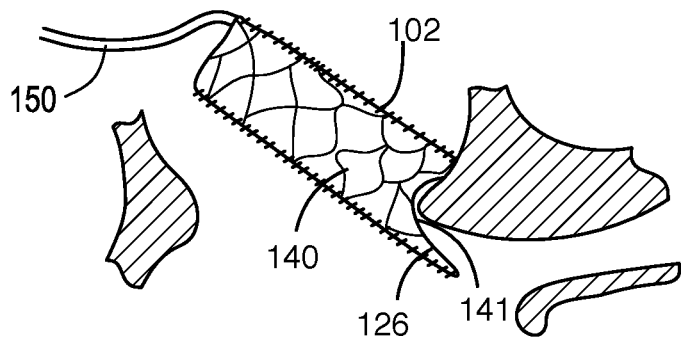
FIG. 8 is an illustration of a valve frame having a braid or laser-cut tubular frame and extended valve sleeve engaging the tissue on the anterior side of the native annulus with the curved distal side-wall of the tubular frame sealing around the native annulus.

FIG. 8 is an illustration of a valve frame 102 having a braid or laser-cut tubular frame 140 engaging the tissue on the anterior side of the native annulus with the curved distal side-wall 141 of the tubular frame 102 sealing around the native annulus. FIG. 8 shows the valve frame 102 held by the steerable secondary catheter 150 at an oblique angle while valve frame 102 function is assessed.

FIG. 9 is an illustration of a heart valve frame prosthesis 101 having a braid or laser-cut tubular frame 102 fully deployed into the tricuspid annulus. The distal side 141 of the valve is shown engaging the tissue on the anterior side of the native annulus with the curved distal side-wall 141 of the tubular frame 102 sealing around the native annulus, and with the proximal side-wall 134 tension-mounted into the posterior side of the native annulus.

FIG. 10 is an illustration of a plan view of a heart valve prosthesis 101 according to the present invention with a valve frame 102 having upper tension arm 128 and lower tension arm 126 mounted on and anchoring to the annulus. FIG. 10 shows lower tension arm/tab 126 extending into the Right Ventricular Outflow Tract (RVOT). The lateral, or side-loaded, delivery of the valve 100 through the inferior vena cava, provides for direct access to the valve annulus without the need to delivery a compressed valve around a right angle turn, as is required for IVC delivery of axially, or vertically loaded, traditional transcatheter valves. FIG. 10 shows one embodiment where a screw or other anchor device 138 is used in conjunction with the tension-mounting method described herein where upper and lower tension arms 126 and 128 on the anterior leaflet side anchor the valve in place, and a secondary anchor element 138 completes the securement of the valve 101 in the annular site.

FIG. 10 shows polyester mesh covering 108 a valve tubular frame 102 encircling an inserted collapsible flow control sleeve 104. FIG. 10 also shows the frame 102 having Nitinol wire frame cells 103 in diamond shapes with a biocompatible covering 108. In one embodiment, the frame 102 may have a pericardial material on top and a polyester material, e.g. surgical Dacron®, underneath to be in contact with the native annulus and promote ingrowth.

FIG. 11 is an illustration of a plan view of another embodiment of a heart valve prosthesis according to the present invention with a valve frame 102 having a distal upper tension arm 128 and lower tension arm 126 mounted on, and anchored to, the anterior leaflet side of the native annulus, and having a mechanical anchor element, e.g. proximal sealing cuff, 130 for anchoring on the posterior and septal side of the native annulus. The sealing cuff 130 may be a short tab on the posterior side of the valve frame or may be a semi-circular or circular collar or cuff that engages the atrial floor to seal the annulus from perivalvular leaks.

FIG. 12 is an illustration of a plan view of another embodiment of a valve frame prosthesis according to the present invention with a valve frame having a distal upper and lower tension arm mounted on, and anchored to, the anterior leaflet side of the native annulus, and having a mechanical anchor element, e.g. hourglass annular seal, 132 for anchoring on the posterior and/or septal side of the native annulus. The hourglass, or concave, sealing cuff 132 may be only a short segment on the posterior side of the valve or may be a semi-circular or circular combined upper and lower collar or cuff that engages the atrial floor and the ventricular ceiling to seal the annulus from perivalvular leaks. This embodiment may also include embodiments having a partial collar. This embodiment may be used in conjunction with other anchoring elements described herein.

FIG. 13 is an illustration of a PLAN view of a low-profile, e.g. 10 mm in height, wire loop embodiment of the valve frame 140 as an annulus support loop and an upper and lower tension arm 142, 144 formed as a unitary or integral part connected by joint 143, and covered with a biocompatible material 108. This embodiment shows how a low profile, side-loaded valve frame 140 can having a very large diameter, 40-80 mm, with requiring an excessively large delivery catheter, as would be required by a large diameter valve that is delivered using the traditional, vertical or axial, orientation. FIG. 13 shows the frame 140 with flexible conduit as a flow control element 104 mounted on the frame 140.

FIG. 14 is an illustration of a TOP view of a low-profile, e.g. 10 mm in height, wire loop embodiment of the valve frame prosthesis 140 as an annulus support loop with atrial collar 146, an upper and lower tension arm 142, 144 formed as a unitary or integral part, an inner two-panel conical valve sleeve 110, and covered with a biocompatible material 115. FIG. 14 shows the inner two-panel sleeve 110 and the reciprocating collapsible aperture 156 at the lower end for delivering blood to the ventricle.

FIG. 15 is an illustration of a BOTTOM view of a low-profile, e.g. 10 mm in height, wire loop embodiment of the valve frame 140 as an annulus support loop with atrial collar 146, an upper and lower tension arm 142, 144 formed as a unitary or integral part, an inner two-panel conical valve sleeve 110, and covered with a biocompatible material 115. FIG. 15 shows a PLAN view of the inner two-panel sleeve 110 and the collapsible terminal aperture 156 at the ventricular side.

FIG. 16 is an illustration of a compressed and elongated wire loop embodiment of the valve frame disposed within a delivery catheter 118 in a rolled/roll compressed configuration 176, and having an ring shaped tubular frame 102 with braid/laser-cut 104 and an upper and lower tension arm 142, 144 formed with joint 143 as a unitary or integral part. FIG. 16 illustrates how a large diameter valve frame, using side-loading, can be delivered.

FIG. 17 is an illustration of a compressed and elongated wire loop embodiment of the valve frame prosthesis partially ejected, and partially disposed within, a delivery catheter 118 and frame 102 as an annulus support loop and an upper and lower tension arm 142, 144 formed as a unitary or integral part. FIG. 17 shows how a valve frame can be partially delivered for positioning in the annulus. The lower tension arm 144 can be used to navigate through the tricuspid leaflets and chordae tendinae while the valve body, the tubular frame, 102 is still within the steerable IVC delivery catheter 118.

FIG. 18 is an illustration of a plan view of a valve frame 102 partially mounted within the valve annulus. By using the side-loaded valve frame 102 of the present invention, the distal side of the prosthesis 142, 144 can be mounted against the anterior aspect of the native annulus, and valve frame function can be assessed. By allowing two pathways for blood flow, the first through the native valve near the posterior leaflet, and the second through the central aperture of the prosthetic valve frame, a practitioner can determine if the heart is decompensating or if valve frame function is less than optimal.

FIG. 19 is an illustration of a plan view of a valve frame prosthesis 101 completely seated within the valve annulus. FIG. 19 shows that the valve frame 102 can be secured in place once the valve function assessment shows that the deployment is successful. Importantly, since the valve frame is a low-profile valve, and fits easily within a standard, e.g. 8-12 mm, delivery catheter without requiring the forceful loading of typical transcatheter valves, the side-loading valve frame can be easily retrieved using the same delivery catheter that is used to deploy the valve frame. FIG. 19 also shows upper and lower tension arm 142, 144 conforming to the native annulus, proximal sealing cuff 130 anchoring and sealing the postero-septal/proximal side, and commercial valve 218 or leaflet sleeve 110 mounted within the frame 102.

FIG. 20 is an illustration of a plan view of a native right atrium of a human heart, and shows the superior vena cava (SVC), the inferior vena cava (IVC), the right atrium (RA), the tricuspid valve and annulus (TCV), the anterior leaflet (A), the posterior leaflet (P), the septal leaflet (S), the right ventricle (RV), and the right ventricular outflow tract (RVOT).

FIG. 21 is an illustration of a valve frame according to the present invention being delivered to tricuspid valve annulus. FIG. 21 shows wire-frame lower tension arm 144 ejected from the delivery catheter 118 and being directed through the annulus and towards the right ventricular outflow tract. FIG. 21 shows an embodiment of an accordion-compressed low-profile valve frame 122 and shows the lower tension arm directed towards the anterior leaflet for placement into the RVOT.

FIG. 22 is an illustration of a valve frame according to the present invention being delivered to tricuspid valve annulus. FIG. 22 shows wire-frame lower tension arm 144 and upper tension arm 142 ejected from the delivery catheter 118, the lower tension arm directed through the annulus and into the right ventricular outflow tract, and the upper tension arm staying in a supra-annular position, and causing a passive, structural anchoring of the distal side of the valve about the annulus. FIG. 22 also shows steerable anchoring catheter 150 attached to a proximal anchoring tab 152. While the valve frame is held in a preseating position, the valve frame can be assessed, and once valve frame function and patient conditions are correct, the steerable anchoring catheter can push the proximal side of the valve frame from its oblique angle, down into the annulus. The steerable anchoring catheter can then install one or more anchoring elements 152.

FIG. 23 is an illustration of a valve frame prosthesis according to the present invention being delivered to tricuspid valve annulus. FIG. 23 shows the entire valve frame 102 ejected from the delivery catheter 118, the wire-frame lower tension arm 144 directed through the annulus and into the right ventricular outflow tract, and the upper wire-frame tension arm 142 staying in a supra-annular position, and causing a passive, structural anchoring of the distal side of the valve about the annulus, and at least one tissue anchor 152 anchoring the proximal side of the prosthesis into the annulus tissue. FIG. 23 shows how a commercial valve 218 can be secondarily deployed into the opening inner surface 114 of the frame.

FIG. 24 is an illustration of a valve frame according to the present invention being delivered to tricuspid valve annulus. FIG. 24 shows braided/laser cut-frame lower tension arm 126 ejected from the delivery catheter 118 and being directed through the annulus and towards the right ventricular outflow tract, with steerable catheter 150 controlling the valve through attachment to the proximal tab 134.

FIG. 25 is an illustration of a valve frame 102 according to the present invention with inner leaflet sleeve 110 being delivered to tricuspid valve annulus. FIG. 25 shows braided/laser cut-frame lower tension arm 126 and upper tension arm 128 ejected from the delivery catheter 118, the lower tension arm directed through the annulus and into the right ventricular outflow tract, and the upper tension arm staying in a supra-annular position, and causing a passive, structural anchoring of the distal side of the valve frame about the annulus. FIG. 25 also shows delivery catheter 118 with steerable catheter 150 attached to proximal tab 134

FIG. 26 is an illustration of a valve frame prosthesis according to the present invention being delivered to tricuspid valve annulus. FIG. 26 shows the entire braided/laser cut-frame 102 ejected from the delivery catheter 118, the lower tension arm 126 directed through the annulus and into the right ventricular outflow tract, and the upper tension arm 128 staying in a supra-annular position, and causing a passive, structural anchoring of the distal side of the valve frame about the annulus, and at least one tissue anchor anchoring the proximal side of the prosthesis into the annulus tissue. FIG. 26 shows how a commercial valve 218 can be secondarily deployed into the opening 114 of the frame 102. FIG. 26 shows delivery catheter 118 and steerable tool catheter 150 being withdrawn.

FIG. 27 is an illustration of a valve frame according to the present invention being delivered to tricuspid valve annulus and shows step 1 in a valve assessment process. FIG. 27 shows braided/laser cut-frame lower tension arm ejected from the delivery catheter and being directed through the annulus and towards the right ventricular outflow tract.

FIG. 28 is an illustration of a valve frame prosthesis according to the present invention being delivered to tricuspid valve annulus, and shows Step 2 in a valve frame assessment process. FIG. 28 shows braided/laser cut-frame lower tension arm and upper tension arm ejected from the delivery catheter, the lower tension arm directed through the annulus and into the right ventricular outflow tract, and the upper tension arm staying in a supra-annular position, and causing a passive, structural anchoring of the distal side of the valve frame about the annulus. FIG. 28 shows that a steerable anchoring catheter can hold the valve frame at an oblique angle in a pre-attachment position, so that the valve frame can be assessed, and once valve frame function and patient conditions are correct, the steerable anchoring catheter can push the proximal side of the valve frame from its oblique angle, down into the annulus. The steerable anchoring catheter can then install one or more anchoring elements.

FIG. 29 is an illustration of a valve frame prosthesis according to the present invention that has been delivered to tricuspid valve annulus, and shows Step 3 in a valve frame assessment process. FIG. 29 shows the entire braided/laser cut-frame valve frame ejected from the delivery catheter, the lower tension arm directed through the annulus and into the right ventricular outflow tract, and the upper tension arm staying in a supra-annular position, and causing a passive, structural anchoring of the distal side of the valve about the annulus, and at least one tissue anchor anchoring the proximal side of the prosthesis into the annulus tissue. FIG. 29 shows how a commercial valve can be secondarily deployed into the opening of the frame.

FIG. 30 is an illustration of a valve frame according to the present invention in a compressed, intra-catheter phase. The lower and upper tension arms 144, 142 are elongated to the right, and the prosthetic valve frame 102 is shown laterally compressed in the delivery catheter 118. The lateral compression is a function of the use of minimal structural materials, e.g. a minimal valve frame, and the relatively short height of the outer cylindrical frame 102. This lateral delivery provides for very large, e.g. up to 80 mm or more, valve prosthesis' to be delivered. The lateral delivery also avoids the need to perform a 90 degree right turn when delivering a valve using the IVC femoral route. This sharp delivery angle has also limited the size and make up of prior valve prosthesis', but is not a problem for the inventive valve frame herein.

FIG. 31 is an illustration of a profile, or plan, view of a wire-frame embodiment of the valve frame prosthesis according to the present invention in a un-compressed, post-catheter-ejection phase. FIG. 31 shows an embodiment where the upper wire-frame tension arm 142 is attached to the tubular frame 102, but the lower tension arm 144 is shaped in an S-shape and connects only to the upper tension arm 142.

FIG. 32 is an illustration of a profile, or plan, view of a braid or laser-cut frame embodiment of the valve frame prosthesis according to the present invention in a un-compressed, post-catheter-ejection phase. FIG. 32 shows an embodiment where the upper braid or laser-cut tension arm 128 is attached to the upper edge of the tubular frame 102, and the lower tension arm 126 is attached to the lower edge of the tubular frame 102.

FIG. 33 is an illustration of a TOP view of a valve frame prosthesis according to the present invention having covered wire loop for the upper tension arm(s). FIG. 33 shows the tubular frame 102 having an inner leaflets 110 sewn into the central aperture 106, with the two (2) panels extending downward (into the page) in a ventricular direction. FIG. 33 shows the upper tension arms 142 oriented towards the anterior leaflet side of the atrial floor, shown in dashed outline.

FIG. 34 is an illustration of a PLAN view of a valve frame prosthesis according to the present invention having a wire loop construction for the upper 142 and lower 144 tension arms.

FIG. 35 is an illustration of a CUT-AWAY PLAN view of a valve frame prosthesis according to the present invention, and shows a commercial available valve 110 mounted within the inner space defined by the tubular frame.

FIG. 36 is an illustration of a BOTTOM view of a valve frame prosthesis according to the present invention having a covered wire loop for the lower tension arm 144. FIG. 36 shows the tubular frame 102 having an inner leaflets of the independently deployed commercially available valve replacements 110 sewn into the central aperture, with the two (2) panels extending upward (out of the page) in a ventricular direction. FIG. 36 shows the lower tension arm 144 oriented towards the anterior leaflet side of the ventricular ceiling, shown in dashed outline.

FIG. 37 is an illustration of a TOP view of a valve frame according to the present invention having covered braid or laser-cut frame 102 for the upper tension arm 128. FIG. 37 shows the tubular frame 102 having commercial valve 110 sewn into the central aperture, with the two (2) panels extending downward (into the page) in a ventricular direction. FIG. 37 shows the upper tension arm 128 oriented towards the anterior leaflet side of the atrial floor, shown in dashed outline.

FIG. 38 is an illustration of a PLAN view of a valve frame according to the present invention having a braid or laser-cut frame construction 102 for the upper and lower tension arms 128, 126.

FIG. 39 is an illustration of a CUT-AWAY PLAN view of a valve frame according to the present invention, and shows a commercial valve 110 mounted within the inner space defined by the tubular frame 102.

FIG. 40 is an illustration of a BOTTOM view of a valve frame prosthesis according to the present invention having a covered braid or laser-cut frame for the lower tension arm. FIG. 40 shows the tubular frame 102 having leaflets of the commercial valve 110 sewn into the central aperture, with the two (2) panels extending upward (out of the page) in a ventricular direction. FIG. 40 shows the lower tension arm 126 oriented towards the anterior leaflet side of the ventricular ceiling, shown in dashed outline.

FIG. 41 is an illustration of a valve frame prosthesis according to the present invention having a wire loop construction for the tubular frame 102, with two vertical support posts 154 extending down the edge on opposing sides of the sleeve 110. During compression into the delivery catheter 118 (not shown), the posts 154 are engineered to fold horizontally during compression, and to elastically unfold during ejection to deploy the valve sleeve 110.

FIG. 42 is an illustration of a CUT-AWAY PLAN view of a valve frame prosthesis according to the present invention, and shows a two-post embodiment 154 of the inner commercial valve 110 mounted within the inner space defined by the tubular frame 102.

FIG. 43 is an illustration of a CUT-AWAY PLAN view of a valve frame prosthesis according to the present invention, and shows a three-panel, three-post embodiment of the inner commercial valve mounted within the inner space defined by the tubular frame.

FIG. 44 is an illustration of a TOP view of a valve frame according to the present invention having braid or laser-cut wire frame 102 and shown mounted within a cross-sectional view of the atrial floor at the annulus.

FIG. 45 is an illustration of a BOTTOM view of a valve frame prosthesis according to the present invention having braid or laser-cut wire frame 102 for a lower tension arm 126 and shown mounted within a cross-sectional view of the ventricular ceiling at the annulus. FIG. 45 shows the two panel valve sleeve of the commercial valve 110 in an open position 106, e.g. atrial systole and ventricular diastole. FIG. 41 shows RVOT as a darkened circle.

FIG. 46 is an illustration of a PLAN view of an embodiment of the prosthetic valve frame shown in a compressed configuration within a delivery catheter. FIG. 46 shows the tubular frame wall rolled-over, outwardly, resulting in a 50% reduction in height of the catheter-housed valve. The low profile, side-loaded valve frames of the present invention do not require the aggressive, strut-breaking, tissue-tearing, stitch-pulling forces that traditional transcatheter valves are engineered to mitigate.

FIG. 47 is an illustration of a cross-sectional view of one embodiment of a compressed valve frame within a delivery catheter 118. This cross-sectional end view shows one embodiment of a single-fold compression configuration 174 where the tubular frame wall 102 is rolled-over, outwardly, resulting in a 50% reduction in height, and providing the ability to fit within the inner diameter of a 1 cm (10 mm) delivery catheter.

FIG. 48 is an illustration of a cross-sectional view of another embodiment of a compressed valve frame within a delivery catheter. This cross-sectional end view shows another embodiment of a single-fold compression configuration 174 where the tubular frame wall are folded-over, outwardly, resulting in a 50% reduction in height, and providing the ability to fit within the inner diameter of a 1 cm (10 mm) delivery catheter.

FIG. 49 is an illustration of a cross-sectional view of an embodiment of the prosthetic valve frame to further illustrate how the folding and rolling configurations can be effectuated due to the minimal material requirement of the low-profile, side-loaded valve frame 102.

FIG. 50(a)-(b)-(c) is an illustration of a sequence of a low-profile valve frame being rolled into a configuration for placement within a delivery catheter. Tubular frame 102 has aperture 106 for supporting a leaflet sleeve 110.

FIG. 51 is an illustration of an END-VIEW of a low-profile valve frame that has been longitudinally rolled into a rolled/roll compressed configuration 176 and loaded within a delivery catheter 118, and shows frame 102.

FIG. 52 is an illustration of a rotational lock embodiment of the present invention where the prosthetic valve frame is delivered to the native annulus with an off-set sub-annular tension arm/tab 126 positioned below the native annulus, and an off-set supra-annular tension arm/tab 128 positioned above the native annulus, while the tubular frame 102 is partially rolled off-set from the annular plane along a longitudinal axis.

FIG. 53 is an illustration of a rotational lock embodiment of the present invention where the prosthetic valve frame is delivered to the native annulus with an off-set sub-annular tension arm/tab 126 positioned below the native annulus, and an off-set supra-annular tension arm/tab 128 positioned above the native annulus, while the tubular frame 102 is rolled into functional position parallel to the annular plane. Once the valve is rolled into position, and the tension arms are locked against the sub-annular and supra-annular tissues, the valve can also be further anchored using traditional anchoring elements as disclosed herein.

FIG. 54 is an illustration of a commercial valve that can be mounted within the frame of the present invention.

FIG. 55 is an illustration of a commercial valve that can be mounted within the frame of the present invention 110 having two rigid support posts 154.

FIG. 56 is an illustration of a commercial valve that can be mounted within the frame of the present invention, having a three-panel embodiment.

FIG. 57 is an illustration of a commercial valve that can be mounted within the frame of the present invention, having a three-panel embodiment and having three rigid support posts 154.

FIG. 58 is an illustration of the trans-septal (femoral-IVC) delivery of a low-profile, e.g. 8-20 mm, side-loaded prosthetic MITRAL valve frame shown partially housed within the delivery catheter, and partially ejected for deployment into the native mitral annulus.

FIG. 59 is an illustration of a low-profile, e.g. 8-20 mm, side-loaded prosthetic MITRAL valve frame shown housed within the delivery catheter.

FIG. 60 is an illustration of a low-profile, e.g. 8-20 mm, side-loaded prosthetic MITRAL valve frame shown partially housed within a delivery catheter and partially laterally ejected from the delivery catheter and positioned for deployment against the anterior side of the native mitral annulus.

FIG. 61 is an illustration of a low-profile, e.g. 8-20 mm, side-loaded prosthetic MITRAL valve frame shown ejected from the delivery catheter and positioned against the anterior side of the native mitral annulus.

FIG. 62 is an illustration of a side or plan view of a low-profile, e.g. 8-20 mm, side-loaded prosthetic valve frame shown deployed into the native MITRAL annulus.

FIG. 63 is an illustration of the heart and shows an approximate location of the valves, the left and right atrium, the left and right ventricles, and the blood vessels that enter and exit the chambers of the heart.

FIG. 64 is an illustration of a low-profile, e.g. 8-20 mm, side-loaded valve frame shown housed within the delivery catheter.

FIG. 65 is an illustration of a low-profile, e.g. 8-20 mm, side-loaded valve frame shown partially housed within a delivery catheter and partially laterally ejected from the delivery catheter and positioned for deployment against the anterior side of the native annulus.

FIG. 66 is an illustration of a low-profile, e.g. 8-20 mm, side-loaded valve frame shown ejected from the delivery catheter and positioned against the anterior side of the native annulus.

FIG. 67 is an illustration of a side or plan view of a low-profile, e.g. 8-20 mm, side-loaded valve frame shown deployed into the native annulus of a heart valve.

FIG. 68 is an illustration of a side view of two types of deliverable valves, the first is a self-expanding transcatheter valve, and the second is a commercially-approved transcatheter balloon-expandable prosthetic valve being vertically deployed into the central lumen of the already (laterally, horizontally, orthogonally) deployed valve frame.

FIG. 69 is an illustration of a side view of a commercially-approved transcatheter self-expandable prosthetic valve mounted within the central lumen of the already (laterally, horizontally, orthogonally) deployed valve frame.

FIG. 70 is an illustration of a side view of a commercially-approved transcatheter balloon-expandable prosthetic valve mounted within the central lumen of the already (laterally, horizontally, orthogonally) deployed valve frame.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. An orthogonally delivered transcatheter prosthetic valve frame, the frame comprising:
a tubular frame having a central lumen defined by an inner circumferential surface of the tubular frame, the tubular frame having an outer circumferential surface for engaging native annular tissue,
wherein the tubular frame is compressible to a compressed orthogonal configuration for introduction into the body using a delivery catheter for implanting at a desired location in the body, the compressed orthogonal configuration having a horizontal long-axis oriented at an intersecting angle of between 45-135 degrees to a vertical axis of the central lumen, and expandable to an expanded configuration having a horizontal long-axis oriented at an intersecting angle of between 45-135 degrees to the vertical axis of the central lumen,
wherein the horizontal long-axis of the compressed configuration of the tubular frame is substantially parallel to a length-wise cylindrical axis of the delivery catheter, and
wherein the tubular frame forms a two part framework, a first part having a flared atrial cuff joined to a second part that includes a trans-annular tubular segment having a top edge, wherein the cuff is joined to the trans-annular tubular segment around the circumference of the top edge of the trans-annular tubular segment.

2. The frame of claim 1, wherein the tubular frame is formed of a wire loop or laser-cut wire frame, and the tubular frame is covered with a biocompatible material.

3. The frame of claim 1, wherein the tubular frame has a side profile of a flat cone shape having a diameter R of 40-80 mm, a diameter r of 20-60 mm, and a height of 5-60 mm.

4. The frame of claim 1, wherein the tubular frame has the inner circumferential surface and the outer circumferential surface, the inner circumferential surface and the outer circumferential surface covered with a biocompatible material such that at least one of (i) the inner circumferential surface is covered with pericardial tissue, (ii) the outer circumferential surface is covered with a woven synthetic polyester material, and (iii) both the inner circumferential surface is covered with pericardial tissue and the outer circumferential surface is covered with the woven synthetic polyester material.

5. The frame of claim 1, wherein the tubular frame has a side profile of an hourglass shape having a top diameter R1 of 40-80 mm, a bottom diameter R2 of 50-70 mm, an internal diameter r of 20-60 mm, and a height of 5-60 mm.

6. The frame of claim 1, wherein the central lumen of the tubular frame is configured to receive a flow control component having an internal diameter of 20-60 mm and a height of 10-40 mm, the flow control component having a plurality of leaflets of pericardial material joined to form a rounded cylinder at an inflow end and having a closable aperture at an outflow end.

7. The frame of claim 6, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battens, rigid or semi-rigid panels, and combinations thereof.

8. The frame of claim 1, wherein the tubular frame has a distal lower tension arm forming a portion of the outer circumferential surface and being extendable from a distal side of the tubular frame, the distal lower tension arm formed of wire loop, wire frame, or integrated frame section, extendable from about 10-40 mm away from the tubular frame.

9. The frame of claim 1, wherein the tubular frame has a distal upper tension arm attached to a distal upper edge of the tubular frame, the distal upper tension arm formed of wire loop or wire frame extending from about 2-20 mm away from the tubular frame, and a distal lower tension arm extending from a distal side of the tubular frame, the distal lower tension arm formed of wire loop, wire frame, or integrated frame section, extending from about 10-40 mm away from the tubular frame.

10. The frame of claim 1, further comprising at least one tissue anchor connected to the tubular frame for engaging native tissue.

11. An orthogonally delivered transcatheter prosthetic valve frame, the frame comprising:
a tubular frame having a central lumen defined by an inner circumferential surface of the tubular frame, the tubular frame having an outer circumferential surface for engaging native annular tissue,
wherein the tubular frame is compressible to a compressed orthogonal configuration for introduction into the body using a delivery catheter for implanting at a desired location in the body, the compressed orthogonal configuration having a horizontal long-axis oriented at an intersecting angle of between 45-135 degrees to a vertical axis of the central lumen, and expandable to an expanded configuration having a horizontal long-axis oriented at an intersecting angle of between 45-135 degrees to the vertical axis of the central lumen,
wherein the horizontal long-axis of the compressed configuration of the tubular frame is substantially parallel to a length-wise cylindrical axis of the delivery catheter,
wherein the tubular frame has a distal lower tension arm forming a portion of the outer circumferential surface and being extendable from a distal side of the tubular frame, the distal lower tension arm formed of wire loop, wire frame, or integrated frame section, extendable from about 10-40 mm away from the tubular frame.

12. The frame of claim 11, wherein the tubular frame forms a two part framework, a first part having a flared atrial cuff joined to a second part that includes a trans-annular tubular segment having a top edge, wherein the cuff is joined to the trans-annular tubular segment around the circumference of the top edge of the trans-annular tubular segment.

13. The frame of claim 11, wherein the tubular frame is formed of a wire loop or laser-cut wire frame, and the tubular frame is covered with a biocompatible material.

14. The frame of claim 11, wherein the tubular frame has the inner circumferential surface and the outer circumferential surface, the inner circumferential surface and the outer circumferential surface covered with a biocompatible material such that at least one of (i) the inner circumferential surface is covered with pericardial tissue, (ii) the outer circumferential surface is covered with a woven synthetic polyester material, and (iii) both the inner circumferential surface is covered with pericardial tissue and the outer circumferential surface is covered with the woven synthetic polyester material.

15. The frame of claim 11, wherein the tubular frame in the expanded configuration has a central tube axis that is substantially parallel to the first direction.

16. The frame of claim 11, wherein the central lumen of the tubular frame is configured to receive a flow control component having an internal diameter of 20-60 mm and a height of 10-40 mm, and a plurality of leaflets of pericardial material joined to form a rounded cylinder at an inflow end and having a closable aperture at an outflow end.

17. The frame of claim 16, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battens, rigid or semi-rigid panels, and combinations thereof.

18. The frame of claim 11, wherein the tubular frame has a distal upper tension arm attached to a distal upper edge of the tubular frame, the distal upper tension arm formed of wire loop or wire frame extending from about 2-20 mm away from the tubular frame.

\* \* \* \* \*